US011116497B2

(12) United States Patent
Maisano et al.

(10) Patent No.: US 11,116,497 B2
(45) Date of Patent: Sep. 14, 2021

(54) SUTURE-SECURING DEVICE

(71) Applicant: 4Tech Inc., Waltham, MA (US)

(72) Inventors: Francesco Maisano, Zurich (CH); Hugo Vanermen, Knocke-le-Zoute (BE); Ottavio Alfieri, Brescia (IT); Idan Tobis, Beth Hashmonai (IL); Andrea Guidotti, Zurich (CH); Paolo Denti, Opera (IT)

(73) Assignee: 4Tech Inc., Edina, MN (US)

(*) Notice: Subject to any disclaimer, the term of this patent is extended or adjusted under 35 U.S.C. 154(b) by 241 days.

(21) Appl. No.: 16/242,337

(22) Filed: Jan. 8, 2019

(65) Prior Publication Data
US 2019/0133575 A1     May 9, 2019

Related U.S. Application Data

(60) Continuation of application No. 15/267,769, filed on Sep. 16, 2016, now Pat. No. 10,206,673, which is a
(Continued)

(51) Int. Cl.
*A61B 17/04*     (2006.01)
*A61B 17/064*     (2006.01)
(Continued)

(52) U.S. Cl.
CPC .... *A61B 17/0487* (2013.01); *A61B 17/00234* (2013.01); *A61B 17/0401* (2013.01);
(Continued)

(58) Field of Classification Search
CPC ............ A61B 17/0487; A61B 17/0401; A61B 2017/0414; A61B 2017/0464; A61B 2017/0441; A61B 2017/0443
See application file for complete search history.

(56) References Cited

U.S. PATENT DOCUMENTS

2003/0093096 A1    5/2003    McGuckin, Jr. et al.
2005/0049617 A1*   3/2005    Chatlynne .......... A61B 17/0401
                                                       606/148
(Continued)

FOREIGN PATENT DOCUMENTS

WO      2011004374 A1     1/2011

OTHER PUBLICATIONS

U.S. Appl. No. 13/485,145, filed May 31, 2012, 2013/0325115, U.S. Pat. No. 8,961,594.
(Continued)

*Primary Examiner* — Wade Miles
(74) *Attorney, Agent, or Firm* — UltimatEdge IP Law Group, P.C.; Dean G. Stathakis; Vito A. Canuso, III

(57) ABSTRACT

A suture-securing device includes a first tubular element, shaped to define a first lumen therethrough, and having first and second ends; and a second tubular element, shaped to define a second lumen therethrough, and having first and second ends. The suture-securing device is configured to have (a) an unlocked configuration in which the first end of the second tubular element is disposed closer to the first end of first tubular element than is the second end of the second tubular element, and the sutures are disposable within and slidable through the first and second lumens, and (b) a locking configuration in which the second end of the second tubular element is disposed closer to the first end of first tubular element than is the first end of the second tubular element, and the sutures are inhibited from sliding through the first and second lumens. Other embodiments are also described.

19 Claims, 17 Drawing Sheets

Related U.S. Application Data continuation of application No. 14/584,286, filed on Dec. 29, 2014, now abandoned, which is a division of application No. 13/485,145, filed on May 31, 2012, now Pat. No. 8,961,594.

(51) Int. Cl.
*A61F 2/24* (2006.01)
*A61B 17/00* (2006.01)

(52) U.S. Cl.
CPC .......... *A61B 17/064* (2013.01); *A61F 2/2436* (2013.01); *A61F 2/2445* (2013.01); *A61F 2/2487* (2013.01); *A61B 2017/00243* (2013.01); *A61B 2017/00783* (2013.01); *A61B 2017/0414* (2013.01); *A61B 2017/0441* (2013.01); *A61B 2017/0464* (2013.01); *A61B 2017/0641* (2013.01); *A61F 2220/0016* (2013.01); *A61F 2220/0075* (2013.01); *A61F 2230/0006* (2013.01)

(56) References Cited

U.S. PATENT DOCUMENTS

| | | |
|---|---|---|
| 2007/0021781 A1 | 1/2007 | Jervis et al. |
| 2007/0083235 A1 | 4/2007 | Jervis et al. |
| 2010/0161047 A1* | 6/2010 | Cabiri .................. A61B 17/072 623/2.37 |
| 2011/0040326 A1* | 2/2011 | Wei ...................... A61B 17/083 606/232 |
| 2014/0275865 A1 | 9/2014 | Tammam et al. |

OTHER PUBLICATIONS

U.S. Appl. No. 14/584,286, filed Dec. 29, 2014, 2015/0119979.
U.S. Appl. No. 15/267,769, filed Sep. 16, 2016, 2017/0000474, U.S. Pat. No. 10,206,673.

\* cited by examiner

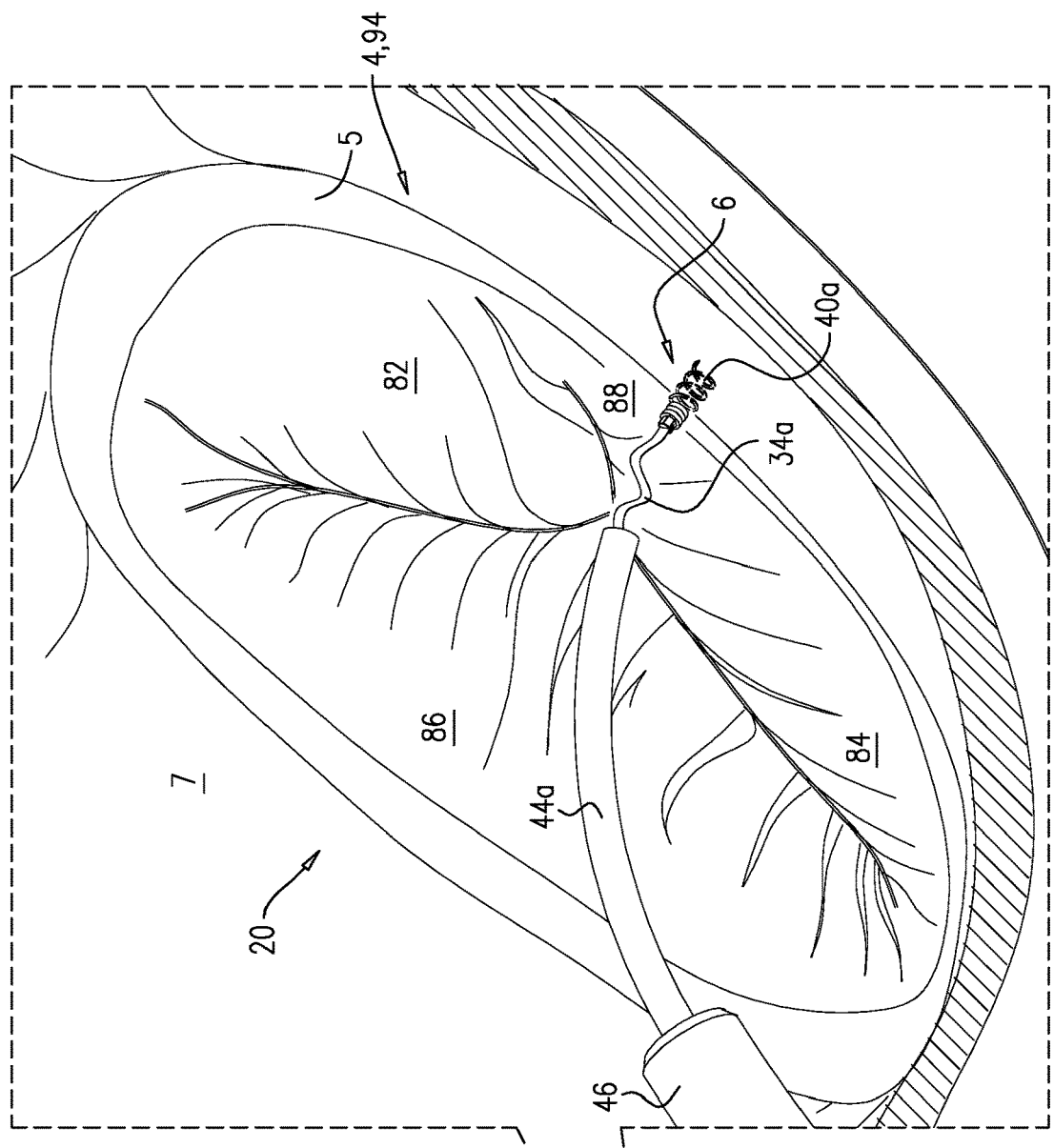
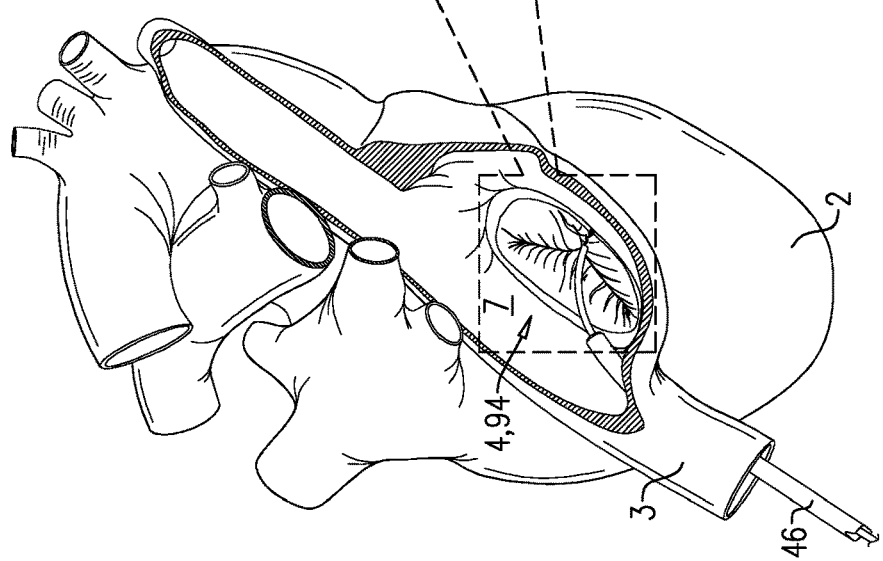
FIG. 3

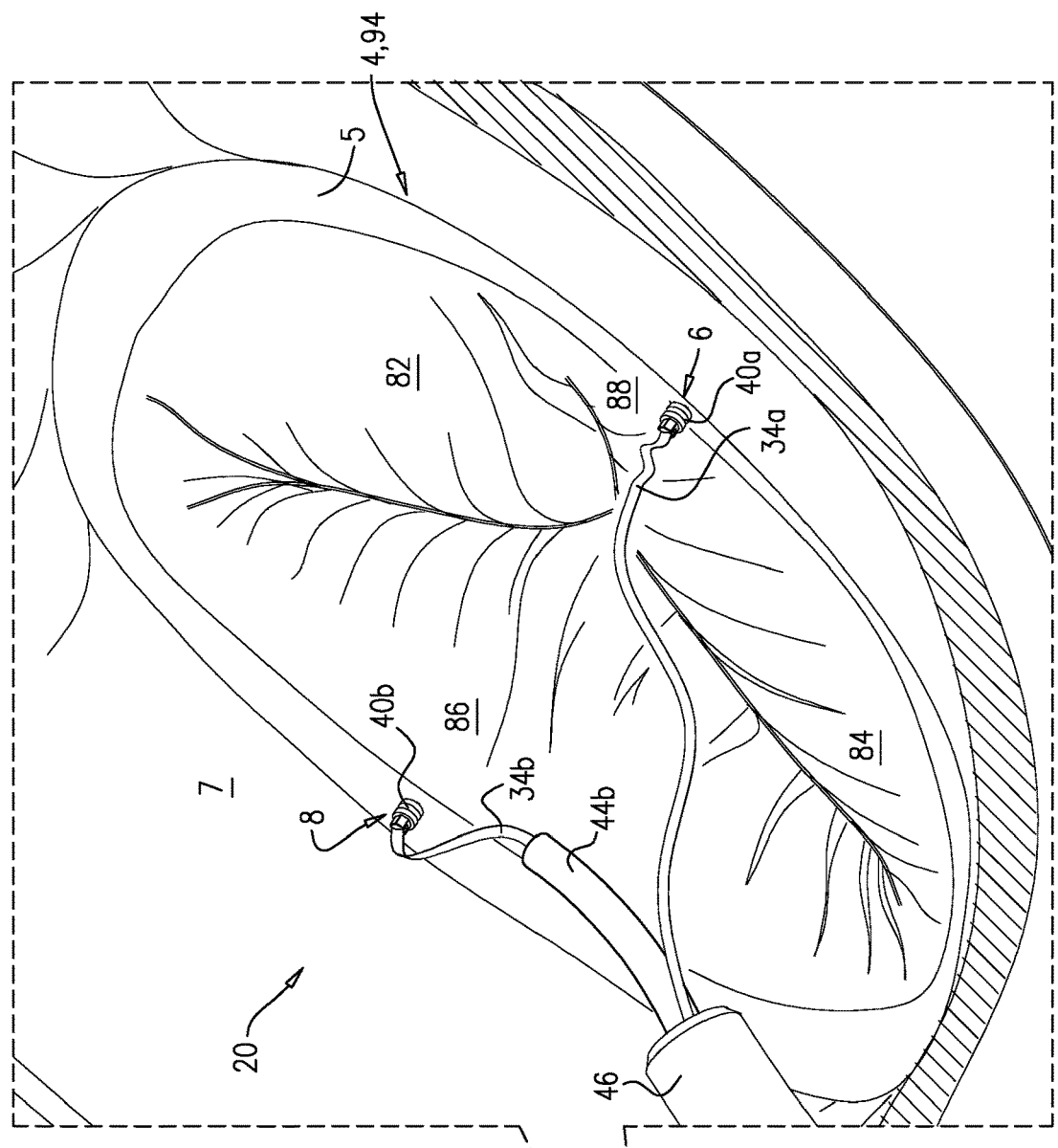
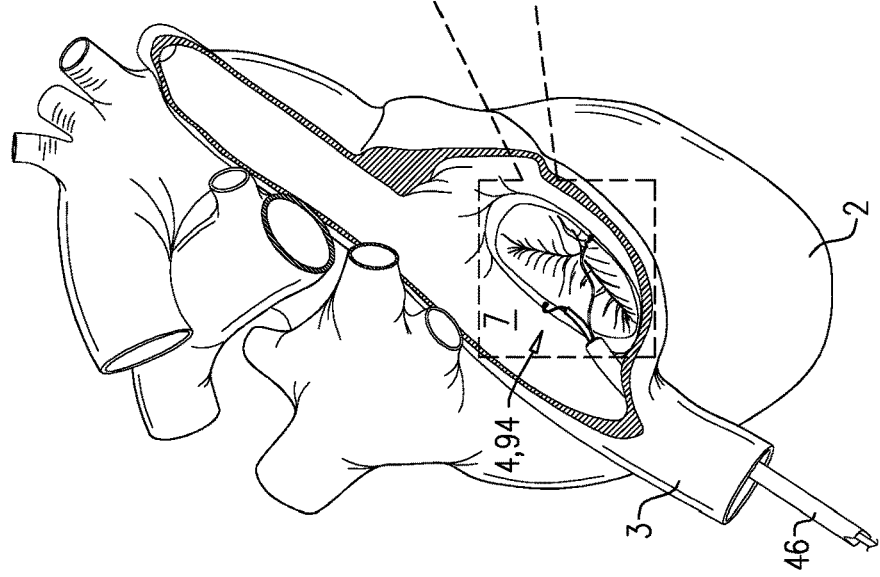
FIG. 4

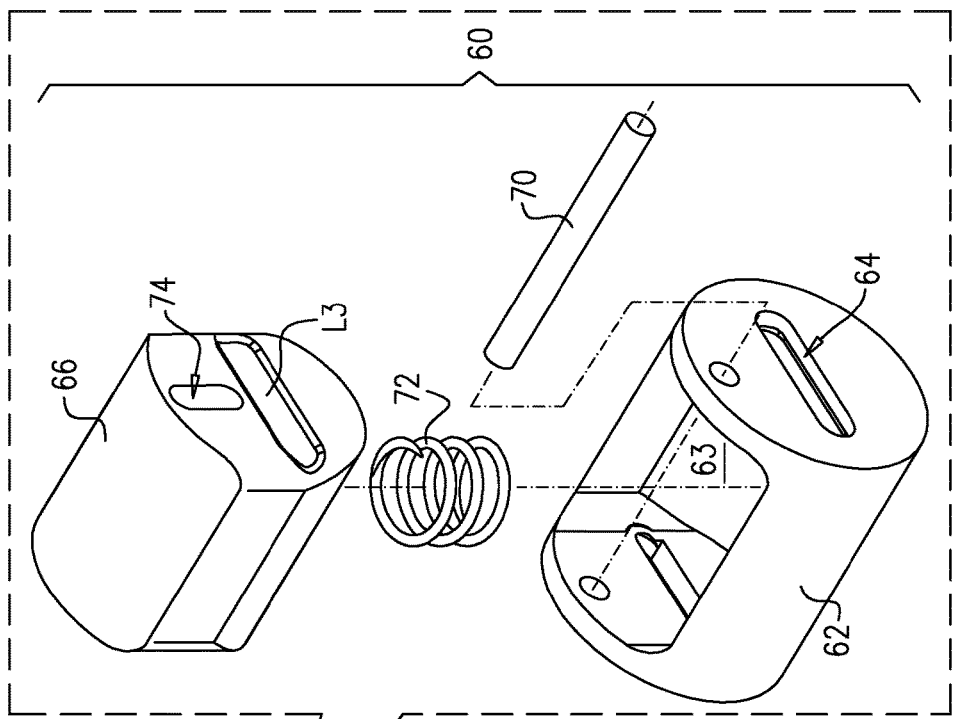
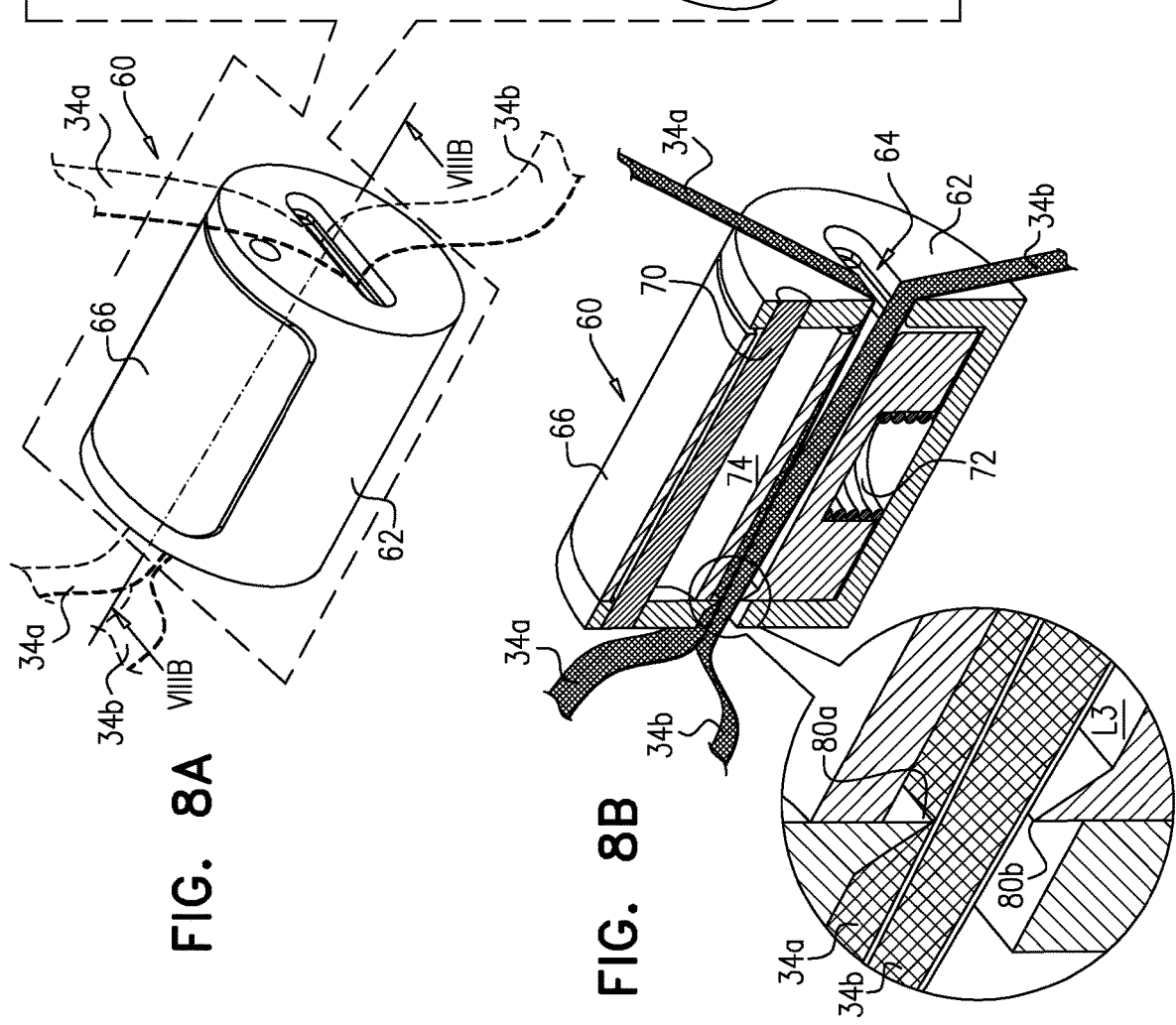
FIG. 8A
FIG. 8B

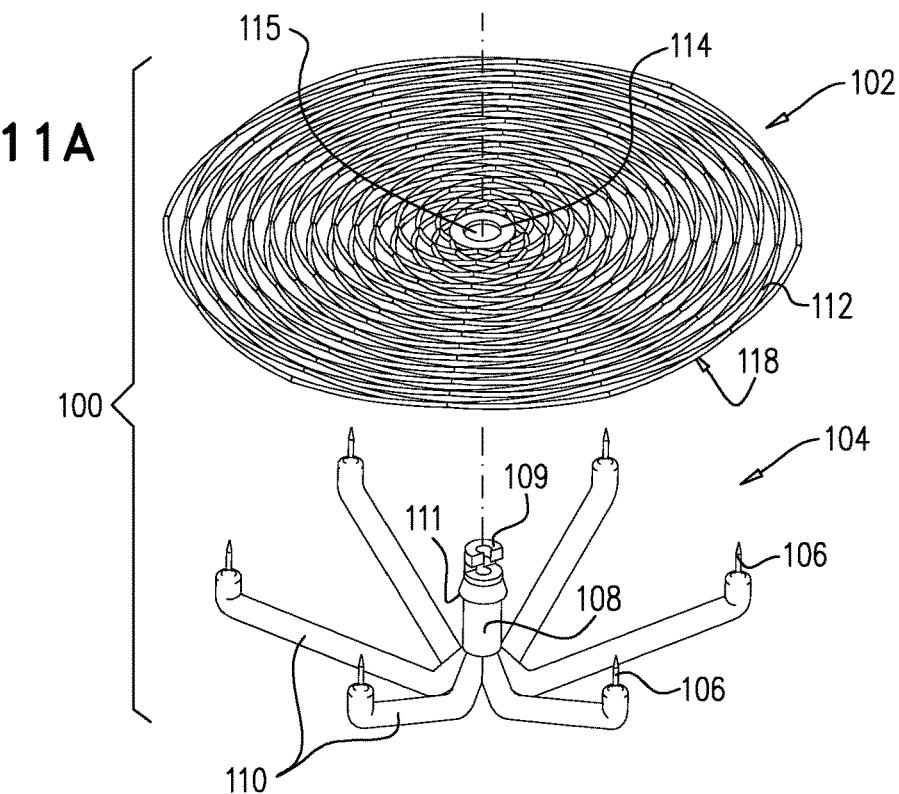
FIG. 11A
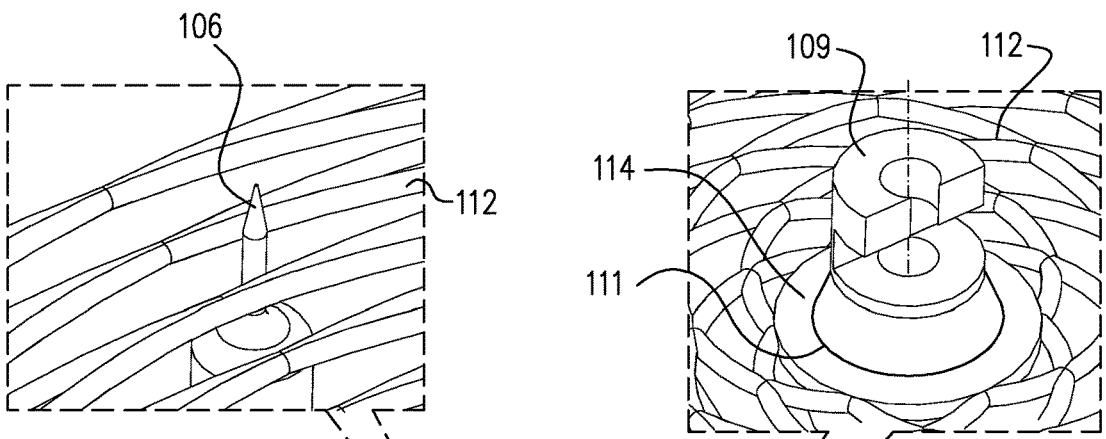
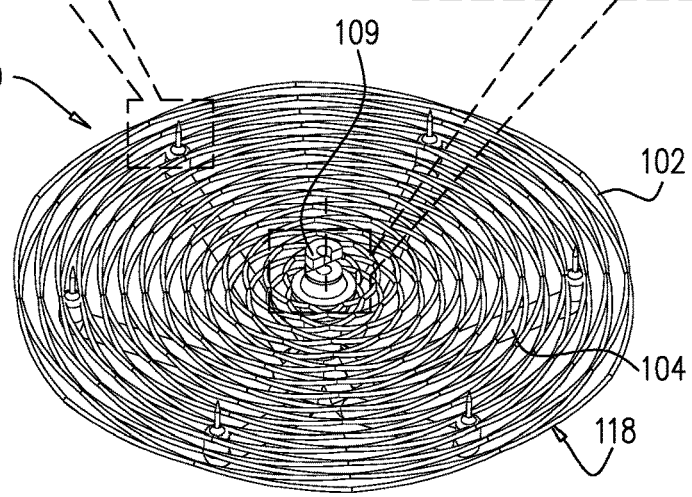
FIG. 11B

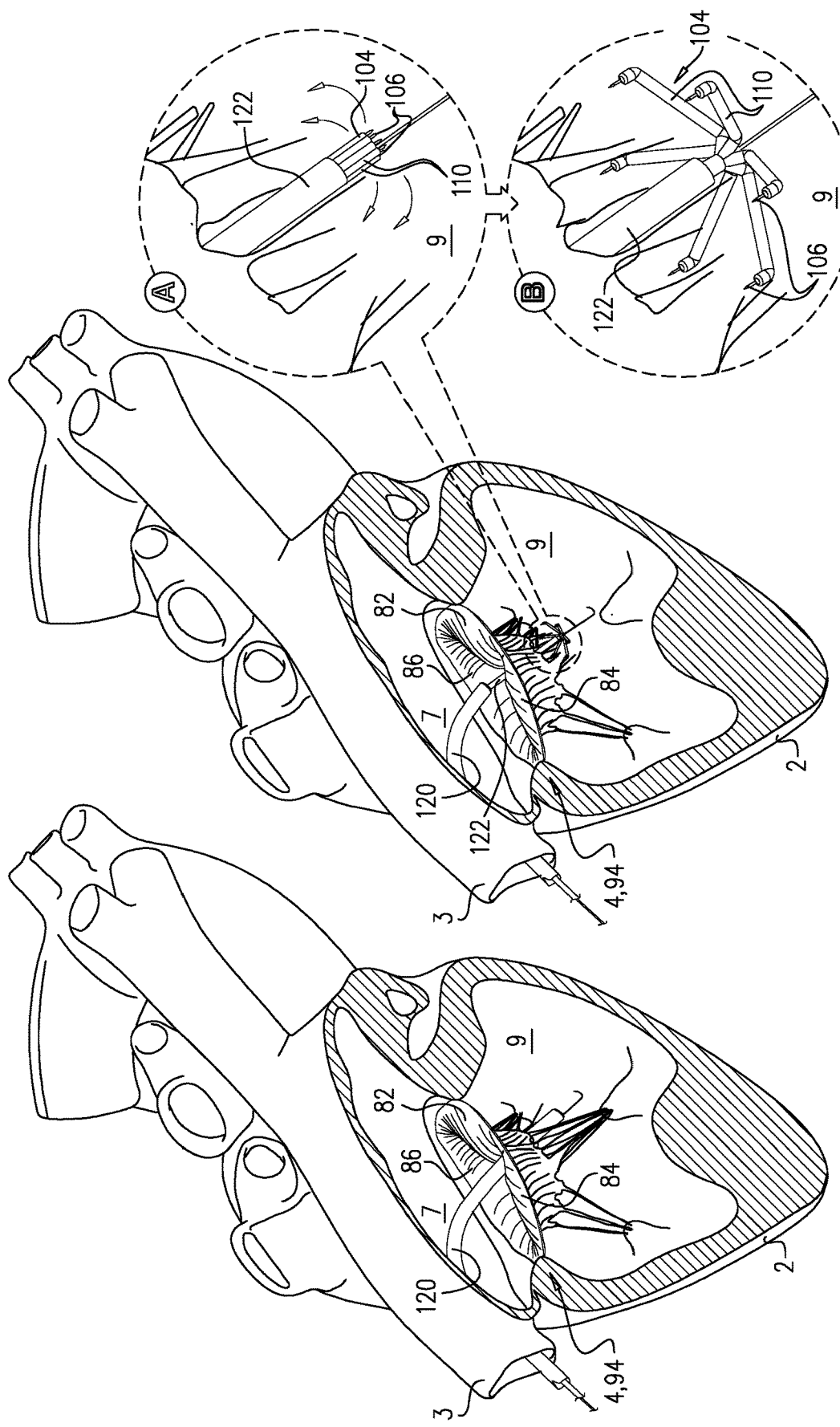

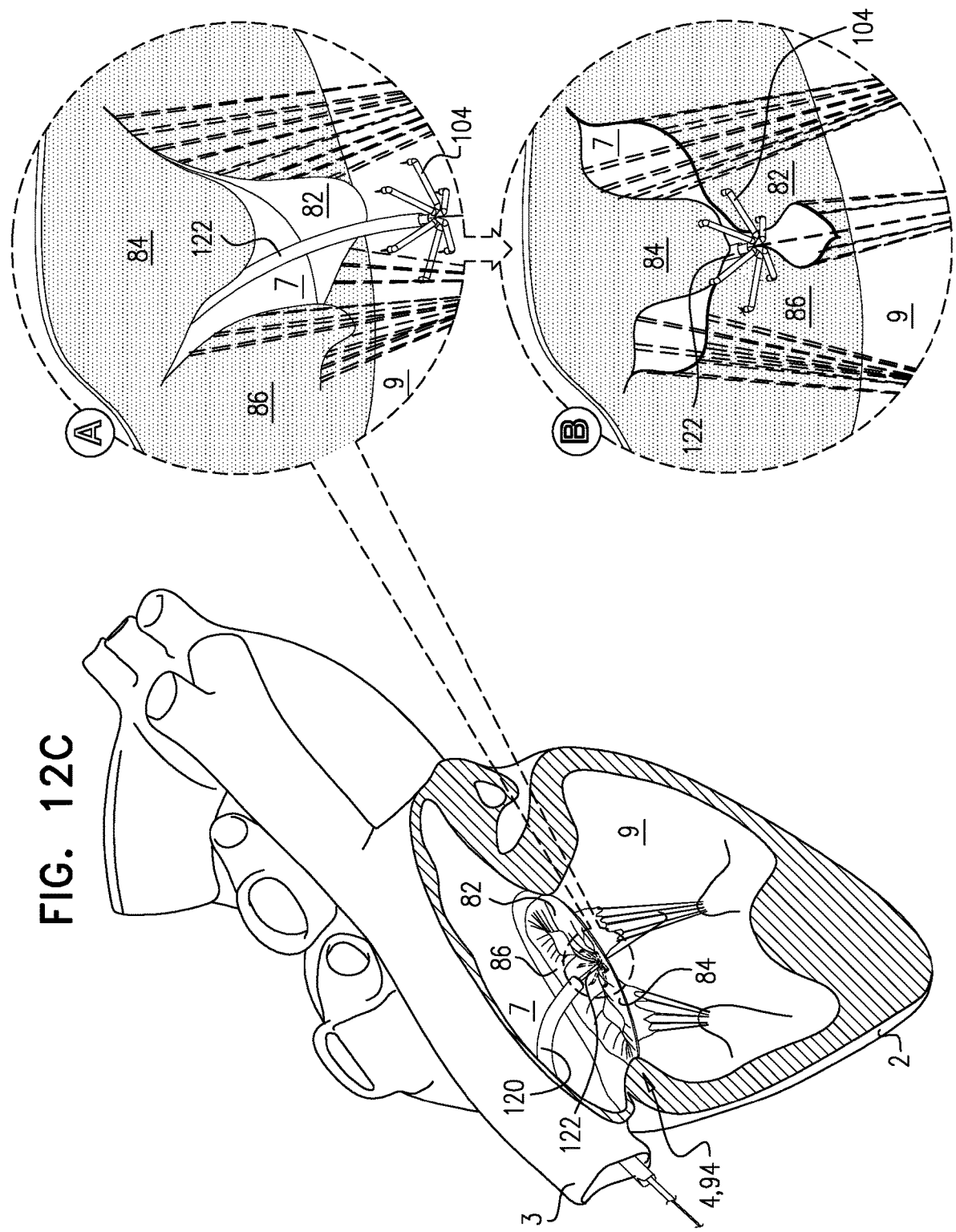

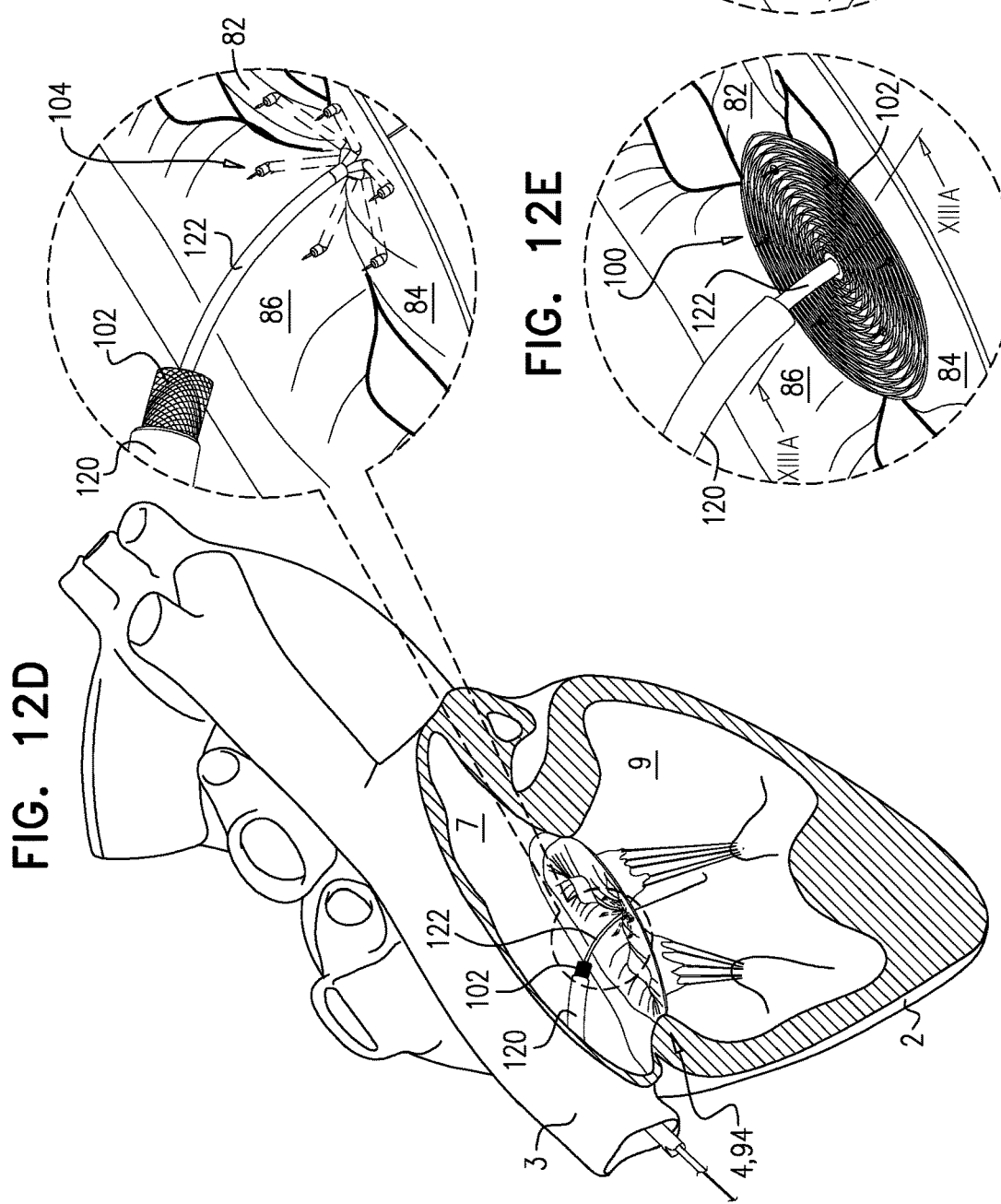

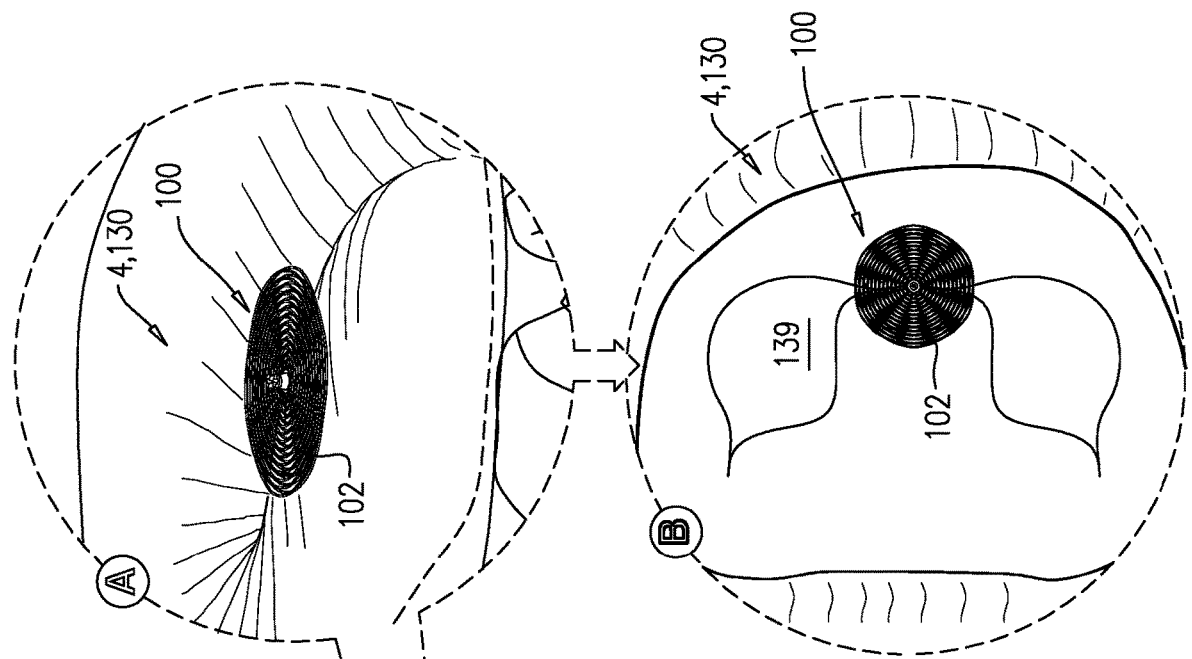
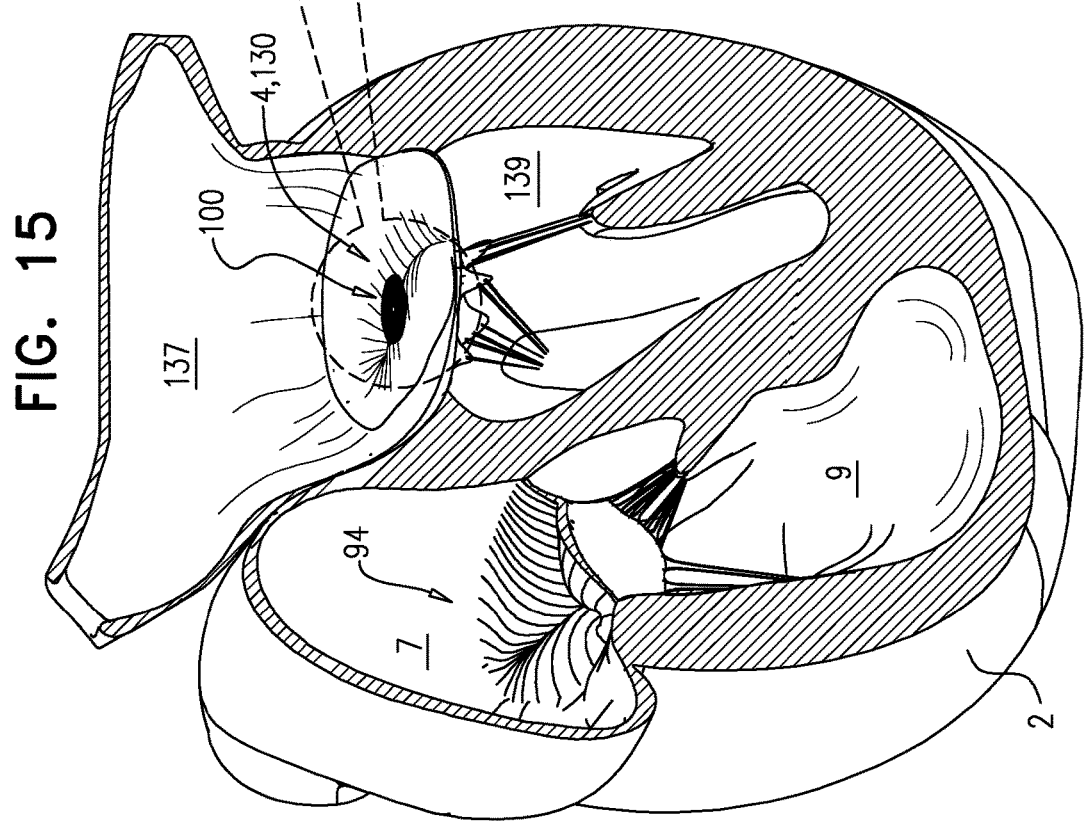
FIG. 15

SUTURE-SECURING DEVICE

CROSS-REFERENCE TO RELATED APPLICATIONS

The present application is a continuation of U.S. application Ser. No. 15/267,769, filed Sep. 16, 2016, now U.S. Pat. No. 10,206,673, which is a continuation of U.S. application Ser. No. 14/584,286, filed Dec. 29, 2014, now abandoned, which is a divisional of U.S. application Ser. No. 13/485,145, filed May 31, 2012, now U.S. Pat. No. 8,961,594.

FIELD OF THE INVENTION

Some applications of the present invention relate in general to surgical techniques. More specifically, some applications of the present invention relate to techniques for securing sutures. More specifically, some applications of the present invention relate to transluminal techniques for securing sutures.

BACKGROUND

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in She United States. Of these, only 8,000 patients undergo tricuspid valve surgeries annually, most of them in conjunction with left heart valve surgeries.

SUMMARY OF THE INVENTION

In some applications of the invention, apparatus and methods are provided for fixedly coupling sutures to each other. For some such applications, the apparatus comprises a suture-securing device that comprises two tubular elements that are movably coupled to each other. For other such applications, the apparatus comprises a suture-securing device that comprises a casing and a core that are movably coupled to each other. Both suture-securing devices described have an unlocked configuration, in which sutures are generally slidable through the device, and a locking configuration, in which the sutures are generally not slidable through the device.

In some applications of the invention, the suture-securing devices are configured to be biased to moving toward the locking configuration thereof, and are retained in the unlocked configuration by a constraint. For such applications, the devices automatically move toward the locking configuration when the constraint is removed.

In some applications of the invention, techniques are provided for using the suture-securing device to repair a heart valve, by fixedly coupling together sutures that are coupled to different parts of the annulus of the valve.

In some applications of the invention, apparatus and methods are provided for repairing a heart valve by sandwiching valve leaflets between a support and a securing element, such that multiple orifices are formed between respective portions of the valve leaflets. Typically, the support is generally disc-shaped, and comprises a wire-mesh. Typically, the securing element comprises a plurality of arms, one end of each arm coupled to a central core, and the other end of each arm coupled to leaflet-piercing elements, which protrude through the valve leaflets and into the wire mesh of the support.

There is therefore provided, in accordance with an application of the present invention, apparatus for use with a heart valve of a patient, the heart valve including at least two leaflets, the apparatus including:

a support, having a leaflet-engaging side, configured to be placed against a first side of the heart valve in a position in which respective portions of the leaflet-engaging side of the support are disposed against respective regions of respective leaflets of the valve; and a plurality of leaflet-piercing elements, deliverable to a second side of the heart valve of the patient, and configured to couple the support to the heart valve by (1) piercing the leaflets of the heart valve from the second side of the heart valve to the first side of the heart valve, and (2) coupling to the support while the support is in the position on the first side of the heart valve.

In an application, the support is flat.

In an application, the support is disc-shaped.

In an application, the support has a delivery configuration in which the support is generally cylindrical, and a deployed configuration in which the support is generally flat.

In an application, the support includes a braided wire mesh.

In an application, the leaflet-piercing elements include straight spikes.

In an application, the leaflet-piercing elements include barbs.

In an application, the leaflet-piercing elements include hooks.

In an application, the leaflet-piercing elements are configured to couple to the support by being configured to protrude into the support.

In an application, the leaflet-piercing elements are configured to couple to the support by being configured to protrude through the support.

In an application, the support is transluminally deliverable to the first side of the heart valve of the patient.

In an application, the leaflet-piercing elements are transluminally deliverable to the second side of the heart valve independently of the support.

In an application, the apparatus further includes a securing element, including:

a core;

two or more arms, an inner end of each arm being coupled to the core, and the arms extending radially outward from the core; and the leaflet-piercing elements, coupled to respective outer ends of each arm.

In an application, the securing element is transluminally deliverable to the second side of the heart valve independently of the support.

In an application, the apparatus is configured such that the leaflet-engaging elements are configured to be coupled to the support by the securing element being configured to be coupled to the support.

In an application, the apparatus is configured such that coupling the leaflet-engaging elements to the support while the support is in the position on the first side of the heart valve, sandwiches the leaflets of the heart valve between the support and the securing element.

In an application, the core defines a coupling portion, configured to couple the core to the support.

In an application, the apparatus is configured such that the coupling of the core to the support facilitates the coupling of the leaflet-piercing elements to the support.

In an application, the support defines an inner perimeter that defines an opening through the support, and the coupling portion is configured to couple the core to the support, by being configured to secure at least part of the coupling portion within the opening.

In an application, the core is configured to extend between the leaflets of the heart valve, from the second side of the heart valve to the first side of the heart valve, such that the coupling portion is couplable to the support at the first side of the heart valve.

In an application, the securing element has a delivery configuration and a deployed configuration, and the outer end of the arms are closer to each other in the delivery configuration than in the deployed configuration.

In an application:

the securing element is disposable within a sheath, and is removable from the sheath, the delivery configuration defines a constrained configuration, the sheath being configured to constrain the securing element in the constrained delivery configuration, the deployed configuration defines an unconstrained configuration, and the securing element is configured to automatically move from the delivery configuration to the deployed configuration when the securing element is removed from the sheath.

There is further provided, in accordance with an application of the present invention, a method for use with a heart valve of a patient, the heart valve including at least two leaflets, the method including:

delivering, to a first side of the heart valve, a support, having a leaflet-engaging side;

delivering, to a second side of the heart valve, a plurality of leaflet-piercing elements;

piercing the leaflets of the valve, from the second side to the first side of the valve, with the leaflet-piercing elements; and coupling the support to the leaflets, such that respective portions of the leaflet-engaging side of the support are disposed against respective regions of respective leaflets, by coupling, at the first side of the valve, the leaflet-piercing elements to the support.

In an application, delivering the support includes delivering a flat support.

In an application, delivering the support includes delivering a disc-shaped support.

In an application, delivering the support includes delivering a support that includes a braided wire mesh.

In an application, delivering the support includes:

percutaneously delivering the support while the support is in a generally-cylindrical delivery configuration thereof, and subsequently, deploying the support into a generally flat deployed configuration thereof.

In an application, coupling the leaflet-piercing elements to the support includes advancing the leaflet-piercing elements into the support.

In an application, coupling the leaflet-piercing elements to the support includes advancing the leaflet-piercing elements through the support.

In an application, delivering the leaflet-piercing elements includes delivering the leaflet-piercing elements independently of delivering the support.

In an application, delivering the leaflet-piercing elements includes delivering, to the second side of the valve, a securing element that includes (1) a core, (2) two or more arms, an inner end of each arm being coupled to the core, and the arms extending radially outward from the core, and (3) the leaflet-piercing elements, coupled to respective outer ends of each arm.

In an application, coupling the leaflet-piercing elements to the support includes coupling the securing element to the support.

In an application, coupling the securing element to the support includes sandwiching the leaflets between the securing element and the support.

In an application, coupling the securing element to the support includes coupling the core to the support, and coupling the core to the support facilitates coupling the leaflet-piercing elements to the support.

In an application, the core defines a coupling portion, and coupling the securing element to the support includes coupling the coupling portion of the core to the support.

In an application, coupling the coupling portion to the support facilitates the coupling of the leaflet-piercing elements to the support.

In an application, the support defines an inner perimeter that defines an opening through the support, and coupling the coupling portion of the core to the support includes securing at least part of the coupling portion within the opening.

In an application, coupling the coupling portion of the core to the support, includes coupling the coupling portion to the support at the first side of the heart valve.

In an application, coupling the coupling portion to the support includes moving at least part of the coupling portion, from the second side of the heart valve, between the leaflets of the heart valve, to the first side of the heart valve.

There is further provided, in accordance with an application of the present invention, apparatus for use with one or more sutures, the apparatus including:

a first tubular element, shaped to define a first lumen therethrough, and having a first end and a second end; and a second tubular element, shaped to define a second lumen therethrough, and having a first end and a second end, the apparatus having:

an unlocked configuration in which:

the first end of the second tubular element is disposed closer to the first end of the first tubular element than is the second end of the second tubular element, and the sutures are disposable within and slidable through the first and second lumens, and a locking configuration in which:

the second end of the second tubular element is disposed closer to the first end of the first tubular element than is the first end of the second tubular element, and the sutures are inhibited from sliding through the first and second lumens.

In an application, the second tubular element has a length, from the first end of the second tubular element to the second end of the second tubular element, that is smaller than the cross-sectional diameter of the first lumen.

In an application, the sutures include a first suture and a second suture, and the apparatus having a locking configuration in which the sutures are inhibited from sliding through the first and second lumens, includes the apparatus having a locking configuration in which the first suture is inhibited from moving with respect to the second suture.

In an application, the apparatus is configured such that:

in the unlocked configuration, the second end of the second tubular element is disposed outside of the first lumen, and in the locking configuration, the second end of the second tubular element is disposed within the first lumen.

In an application, the second end of the first tubular element is coupled to the first end of the second tubular element.

In an application, the apparatus is configured such that, when the sutures are disposed within the lumens of the first and second tubular elements, movement of the apparatus from the unlocked to the locking configuration rotates at least a portion of each suture.

In an application, the apparatus is configured such that movement of the apparatus from the unlocked to the locking configuration rotates the second tubular element.

In an application, the first and second tubular elements include a continuous piece of material.

In an application, the first tubular element is shaped such that the first lumen has a cross-sectional diameter that is greater than a cross-sectional diameter of the second lumen.

In an application, the first tubular element is shaped such that the first lumen has a cross-sectional diameter that is more than 1.1 times greater than the cross-sectional diameter of the second lumen.

In an application, the first tubular element is shaped such that the first lumen has a cross-sectional diameter that is less than 1.5 times greater than the cross-sectional diameter of the second lumen.

In an application:
the unlocked configuration includes a constrained configuration, and the locking configuration includes an unconstrained configuration, and
the apparatus is configured to be retained in the constrained unlocked configuration by a constraining force, and to automatically move toward the unconstrained locking configuration when the constraining force is removed.

In an application, the apparatus further includes a constraint, configured to provide the constraining force.

In an application, the constraint includes a rod, disposable in the lumen of at least one of the tubular elements, configured to provide the constraining force by being disposed in the lumen, the constraining force being removable by removing the rod from the lumen.

In an application, the constraint includes a constraining sheath, configured to provide the constraining force by being disposed around at least one of the tubular members, the constraining force being removable by removing the sheath from the at least one of the tubular members.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, movement of the apparatus from the unlocked to the locking configuration sandwiches at least a portion of each suture between the outer surface of the second tubular element and the inner surface of the first tubular element.

In an application, the apparatus includes at least one helical element.

In an application, at least in the unlocked configuration, the apparatus defines a continuous helix from the first end of the first tubular element to the second end of the second tubular element.

In an application, the first tubular element includes a first helical element and the second tubular element includes a second helical element.

In an application, the second end of the first tubular element is coupled to the first end of the second tubular element by a connecting portion.

In an application, the tubular elements and the connecting portion include a continuous piece of material.

There is further provided, in accordance with an application of the present invention, apparatus for use with one or more sutures, the apparatus including:
a first tubular element, shaped to define a first lumen therethrough, and having a proximal end and a distal end; and
a second tubular element, shaped to define a second lumen therethrough, and having a first end and a second end,
the apparatus having:
an unlocked configuration in which:
the second end of the second tubular element is disposed distally to the first end of the second tubular element, and
the sutures are disposable within and slidable through the first and second lumens, and
a locking configuration in which:
the first end of the second tubular element is disposed distally to the second end of the second tubular element, and
the sutures are inhibited from sliding through the first and second lumens.

In an application, the apparatus is configured such that:
in the unlocked configuration, the second end of the second tubular element is disposed outside of the first lumen, and
in the locking configuration, the second end of the second tubular element is disposed within the first lumen.

In an application, the apparatus is configured such that, when the sutures are disposed within the lumens of the first and second tubular elements, movement of the apparatus from the unlocked to the locking configuration rotates at least a portion of each suture.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, movement of the apparatus from the unlocked to the locking configuration sandwiches at least a portion of each suture between the outer surface of the second tubular element and the inner surface of the first tubular element.

There is further provided, in accordance with an application of the present invention, apparatus for use with one or more sutures, the apparatus including:
a first tubular element, shaped to define a first lumen therethrough; and
a second tubular element, coupled to the first tubular element, and shaped to define a second lumen therethrough,
the apparatus having:
an unlocked configuration in which at least a quarter of the second tubular element is disposed outside of the first lumen, and the sutures are disposable within and slidable through the first and second lumens, and
a locking configuration in which at least a quarter of the second tubular element is disposed inside the first lumen, and the sutures are inhibited from sliding through the first and second lumens, and
the apparatus being constrainable in the unlocked configuration by a removable constraining force, and configured to automatically move toward the second configuration when the constraining force is removed.

In an application, the apparatus is configured such that, when the sutures are disposed within the lumens of the first and second tubular elements, movement of the apparatus from the unlocked to the locking configuration rotates at least a portion of each suture.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, movement of the apparatus from the unlocked to the locking configuration sandwiches at least a portion of each suture between the outer surface of the second tubular element and the inner surface of the first tubular element.

There is further provided, in accordance with an application of the present invention, apparatus for use with one or more sutures, the apparatus including:

a first tubular element, shaped to define a first lumen therethrough; and a second tubular element shaped to define a second lumen therethrough, the second tubular element being coupled to the first tubular element at a coupling point, the coupling point being configured to facilitate deflection of the second tubular element around the coupling point, and the apparatus:
 having an unlocked configuration in which the sutures are disposable within and slidable though the first and second lumens, and a locking configuration in which the sutures are inhibited from sliding through the first and second lumens,
 being configured to be constrainable in the unlocked configuration by a constraining force, and
 being configured, when the constraining force is removed, to automatically move from the unlocked configuration to the locking configuration, by the second tubular element deflecting around the coupling point.

In an application, the apparatus is configured such that, when the sutures are disposed within the lumens of the first and second tubular elements, the deflecting of the second tubular element around the coupling point rotates at least a portion of each suture.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, the deflecting of the second tubular element around the coupling point sandwiches at least a portion of each suture between the outer surface of the second tubular element and the inner surface of the first tubular element.

There is further provided, in accordance with an application of the present invention, apparatus for use with one or more sutures, the apparatus including:

a casing, shaped to define a cavity, and one or more openings in which the sutures are disposable;

a core, disposed in the cavity, and shaped to define a lumen in which the sutures are disposable, the apparatus:
 having an unlocked configuration in which the sutures are disposable within and slidable through the openings and the lumen, and a locking configuration in which the sutures are inhibited from sliding through the openings and the lumen,
 being movable from the unlocked configuration to the locking configuration, and
 being configured such that, when the sutures are disposed within the openings and the lumen, and the apparatus moves from the unlocked configuration to the locking configuration, the apparatus (1) cuts the sutures at a cutting site of the apparatus, and (2) becomes coupled to the sutures at a coupling site of the apparatus.

In an application:
 the casing defines two or more openings, the openings being provided along a longitudinal axis of the casing, in the unlocked configuration of the apparatus, the lumen of the core is disposed along the axis, and between the openings, and
 in the locking configuration of the apparatus, the core is disposed with respect to the casing in a manner in which the lumen of the core is not disposed along the axis.

In an application:
 the casing defines two or more openings,
 in the unlocked configuration of the apparatus, the lumen of the core is generally in fluid communication with the openings, and
 in the locking configuration of the apparatus, the lumen of the core is generally not in fluid communication with the openings.

In an application:
 the unlocked configuration includes a constrained configuration, and the locking configuration includes an unconstrained configuration, and
 the apparatus is configured to be retained in the constrained unlocked configuration by a constraining force, and to automatically move toward the unconstrained locking configuration when the constraining force is removed.

In an application, the apparatus further includes a constraint, configured to provide the constraining force.

In an application, the constraint includes a constraining sheath.

In an application, the cutting site includes at least one cutting edge, and the apparatus is configured to cut the sutures by pushing the sutures against the cutting edge.

In an application:
 the at least one cutting edge includes first and second cutting edges,
 the casing is shaped to define the first cutting edge, and the core is shaped to define the second cutting edge.83. A method for use with one or more sutures at an anatomical site of a patient, the method including:

delivering, to a vicinity of the anatomical site, apparatus that includes (1) a first tubular element, shaped to define a first lumen therethrough, and having a first end and a second end, and (2) a second tubular element, shaped to define a second lumen therethrough, and having a first end and a second end;

sliding the apparatus over at least part of the sutures while the apparatus is in an unlocked configuration thereof in which (1) the first end of the second tubular element is disposed closer to the first end of the first tubular element than is the second end of the second tubular element, and (2) the sutures are slidable through the first and second lumens; and securing the apparatus to the sutures by moving the apparatus into a locking configuration thereof in which: (1) the second end of the second tubular element is disposed closer to the first end of the first tubular element than is the first end of the second tubular element, and (2) the sutures are inhibited from sliding through the first and second lumens.

There is further provided, in accordance with an application of the present invention, a method for use with one or more sutures at an anatomical site of a patient, the method including:

delivering, to a vicinity of the anatomical site, apparatus that includes (1) a first tubular element, shaped to define a first lumen therethrough, and having a first end and a second end, and (2) a second tubular element, shaped to define a second lumen therethrough, and having a first end and a second end;

sliding the apparatus over at least part of the sutures while the apparatus is in an unlocked configuration thereof in which (1) the first end of the second tubular element is disposed closer to the first end of the first tubular element than is the second end of the second tubular element, and (2) the sutures are slidable through the first and second lumens; and subsequently inhibiting the sutures from sliding through the first and second lumens by moving the apparatus into a locking configuration in which the second end of the second tubular element is disposed closer to the first end of the first tubular element than is the first end of the second tubular element.

In an application, in the unlocked configuration, the second end of the second tubular element of the apparatus is disposed outside of the first lumen, and moving the apparatus into the locking configuration includes moving the second end of the second tubular element into the first lumen.

In an application, moving the apparatus into the locking configuration includes moving at least a quarter of the second tubular element into the first lumen.

In an application, moving the apparatus into the locking configuration includes sandwiching at least a portion of each suture between an outer surface of the second tubular element and an inner surface of the first tubular element.

In an application, the apparatus is configured to be constrained in the unlocked configuration by a constraining force, and moving the apparatus into the locking configuration includes removing the constraining force.

In an application, removing the constraining force includes removing, from the lumen of at least one of the tubular elements, a rod that is (1) disposed in the lumen of the least one of the tubular elements, and (2) configured to provide the constraining force.

In an application, removing the constraining force includes removing, from around at least one of the tubular elements, a constraining sheath that is (1) disposed around the at least one of the tubular elements, and (2) configured to provide the constraining force.

In an application, moving the apparatus into the locking configuration includes rotating the second tubular element.

In an application, the first tubular element is coupled to the second tubular element via a coupling point, and rotating the second tubular element includes deflecting the second tubular element around the coupling point.

There is further provided, in accordance with an application of the present invention, a method for use with one or more sutures at an anatomical site of a patient, the method including:

delivering, to a vicinity of the anatomical site, apparatus that includes (1) a casing, shaped to define a cavity, and one or more openings in which the sutures are disposable, and (2) a core, disposed in the cavity, and shaped to define a lumen in which the sutures are disposable;

sliding the apparatus over at least part of the sutures while the apparatus is in an unlocked configuration thereof, in which the sutures are slidable through the openings and the lumen; and subsequently, by moving the apparatus into a locking configuration thereof, simultaneously (1) inhibiting the sutures from sliding through the lumen by coupling the apparatus to the sutures at a coupling site of the apparatus, and (2) cutting the sutures with one or more cutting edges at a cutting site of the apparatus.

In an application, the apparatus is configured to be constrained in the unlocked configuration by a constraining force, and moving the apparatus into the locking configuration includes removing the constraining force.

In an application, removing the constraining force includes removing, from around at least part of the core, a constraining sheath that is (1) disposed around the at least part of the core, and (2) configured to provide the constraining force.

For some applications, techniques described herein are practiced in combination with techniques described in one or more of the references cited in the Background section and Cross-references section of the present patent application.

BRIEF DESCRIPTION OF THE DRAWINGS

FIGS. 3-7 are schematic illustrations of stops in the use of the apparatus of FIGS. 1A-B and 2A-B to repair a cardiac valve, in accordance with some applications of the invention;

FIGS. 8A-B and 9A-B are schematic illustrations of a suture-securing device, in accordance with some applications of the invention;

FIGS. 11A-B are schematic illustrations of apparatus for repairing a heart valve, in accordance with some applications of the invention;

FIGS. 12A-F, 13A-B and 14 are schematic illustrations of the use or the apparatus of FIGS. 11A-B to repair a heart valve, in accordance with some applications of the invention; and FIG. 15 is a schematic illustration of the apparatus of FIGS. 11A-B having been used to repair a heart valve, in accordance with some applications of the invention.

DETAILED DESCRIPTION OF EMBODIMENTS

Reference is made to FIGS. 1A-B and 2A-B, which are schematic illustrations of apparatus 20, comprising a suture-securing device 22, in accordance with some applications of the invention. Device 22 has an unlocked configuration in which one or more sutures are generally slidable through the device, and a locking configuration in which the sutures are generally not slidable through the device, and is movable from the unlocked configuration to the locking configuration.

Figure 1A:
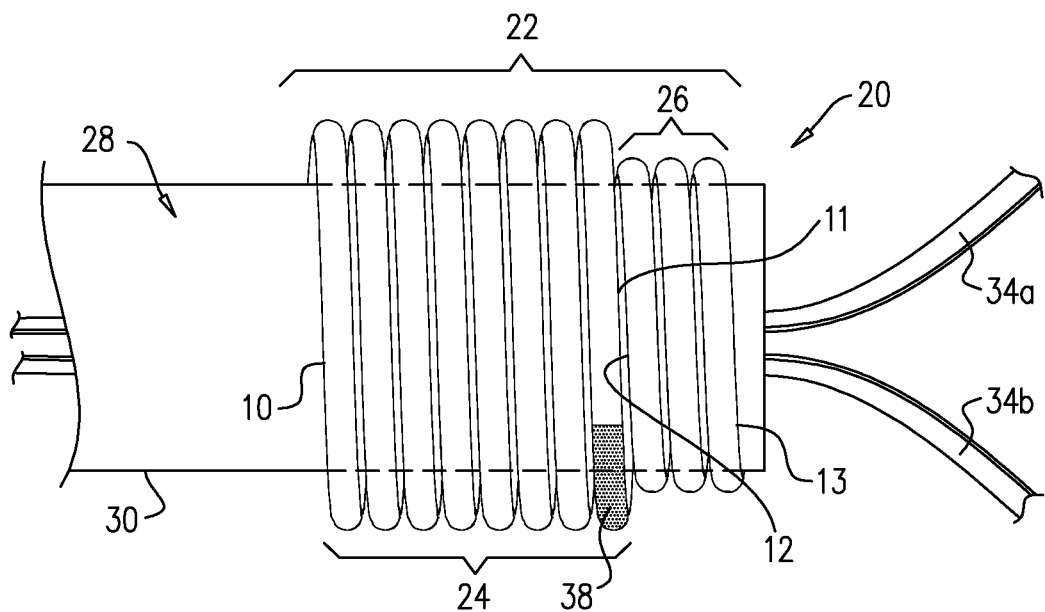
FIGS. 1A-B and 2A-B are schematic illustrations of apparatus comprising a suture-securing device, in accordance with some applications of the invention.
Figure 1B:
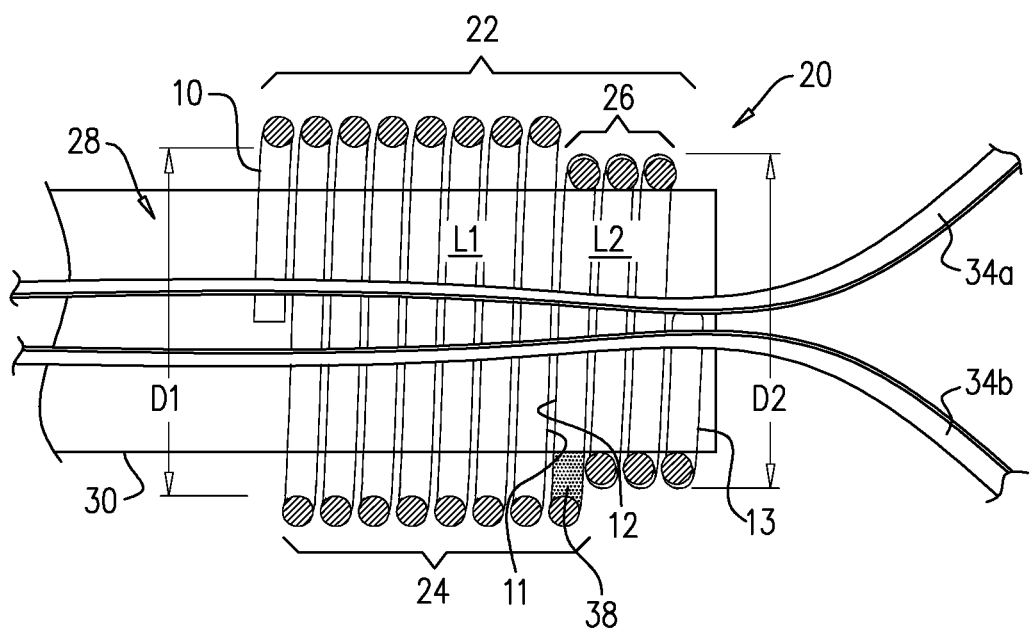

FIGS. 1A-B show device 22 in the unlocked configuration thereof. FIG. 1A shows a side view of device 22 being used with two sutures 34a and 34b, and FIG. 1B shows a cutaway view of the same. It is to be noted that, although device 22 is shown being used with two individual sutures, the device may be used with two portions of the same suture (e.g., the suture is looped), and/or with more or fewer sutures (e.g., to secure the device and/or an element coupled thereto, to a particular point on a single suture). It is to be further noted that, although sutures 34a and 34b are shown as ribbon-like sutures (e.g., having a generally rectangular cross-section), any suitable type of suture, as is known in the art, may be used.

Device 22 comprises a first tubular element 24, which is shaped to define a first lumen L1, a first end 10 and a second end 11, and a second tubular element 26, which is shaped to define a second lumen, a first end 12 and a second end 13. Typically, second tubular element 26 is narrower than first tubular element 24. That is, lumen L2 typically has a smaller transverse cross-sectional area than does lumen L1. Typically, the second tubular element has an outer edge that has a diameter D2 that is smaller than a diameter D1 of an inner edge of the first tubular element.

For some applications of the invention, diameter D1 is more than 1.1 times greater and/or less than 1.5 times greater than diameter D2. Typically, second tubular element 26 has a longitudinal length (i.e., from first end 12 to second end 13) that is smaller than diameter D1 of first tubular element 24, e.g., so as to facilitate rotation of the second tubular element within lumen L1 of the first tubular element.

Typically, device 22 is used in catheter-based procedures or minimally-invasive procedures, and is positioned with respect to the operating physician such that second tubular element 26 is distal to first tubular element 24. Alternatively, the device is positioned with respect to the physician such that the first tubular element is distal to the second tubular element. For some applications, device 22 may be used in a surgical procedure, e.g., an open-heart procedure.

In the unlocked configuration of device 22, the first and second tubular elements are typically disposed end to end. That is, in the unlocked configuration of device 22, one or more of the following are typically true:

(1) first end 12 of the second tubular element is disposed closer to first end 10 of the first tubular element than is second end 13 of the second tubular element, (2) second end 13 of the second tubular element is disposed distally (i.e., with respect to the operating physician) to first end 12 of the second tubular element, and (3) at least a quarter (e.g., all) of second tubular element 26 is disposed outside of lumen L1 of the first tubular element.

In the unlocked configuration, sutures 34a and 34b are slidable through device 22, i.e., through lumens L1 and L2 of tubular elements 24 and 26. That is, in the unlocked configuration, the device is slidably coupled to the sutures, i.e., is slidable over the sutures. Typically, device 22 is delivered to an anatomical site (e.g., in a vicinity of a site being treated) with sutures 34a and 34b pre-threaded through the device.

Typically, and as shown in FIGS. 1A-B, device 22 comprises at least one helical element, e.g., a coil. For example, and as shown in FIGS. 1A-B, tubular elements 24 and 26 may be defined by at least one helix. Further typically, device 22 comprises a continuous piece of material. For example, device 22 may be fabricated from a single elongate piece of material, such as a wire, that has been shaped to define tubular elements 24 and 26 (e.g., by being shaped to define a first helix that defines tubular element 24, and a second helix that defines tubular element 26). Typically, the material comprises a metal such as, but not limited to, stainless steel, titanium, nickel titanium (Nitinol), nickel cobalt, and/or cobalt chrome. For some applications, the material comprises a polymer and/or a resin. Further typically, and as described hereinbelow with reference to FIGS. 2A-B, the material comprises a shape-memory material.

Helical elements 24 and 26 are typically coupled by a connecting portion 38, which facilitates movement of device 22 from the unlocked configuration to the locking configuration. For some applications in which tubular elements 24 and 26 are defined by helices and comprise a single piece of material, connecting portion 38 also comprises the single piece of material. That is, for such applications, device 22, comprising connecting portion 38, comprises a single piece of material.

Figure 2A:
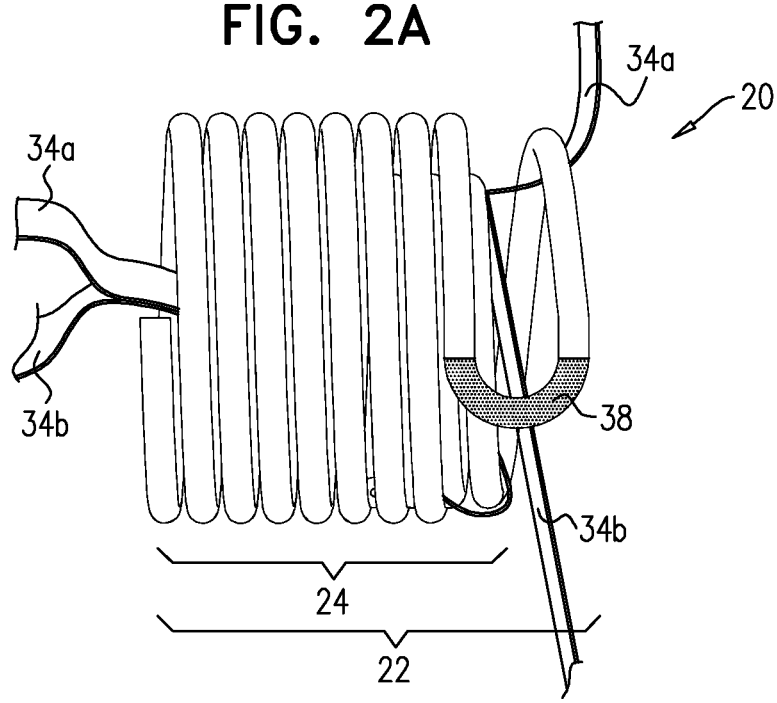
Figure 2B:
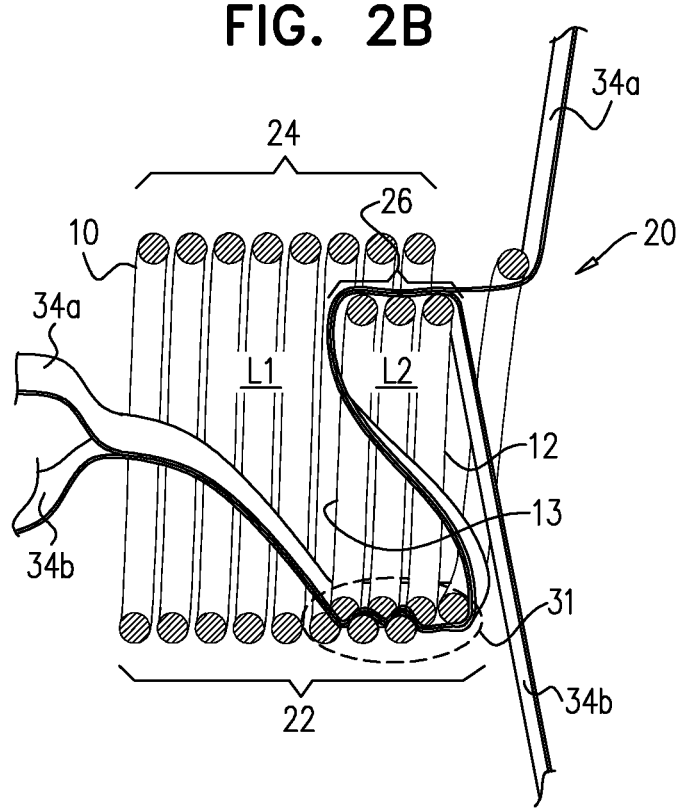

FIGS. 2A-B show device 22 in the locking configuration thereof, i.e., after having moved into the locking configuration. FIG. 2A shows a side view of device 22 being used with two sutures 34a and 34b, and FIG. 2B shows a cutaway view of the same. In the locking configuration of device 22, second tubular element 26 is oriented at about 180 degrees compared to its position in the unlocked configuration of the device. That is, when device 22 moved from the unlocked to the locking configuration, the second tubular element rotates and/or is deflected around an axis that is generally orthogonal to a longitudinal axis from first end 10 of the first tubular element to second end 13 of the second tubular element. Typically, and as shown in FIGS. 2A-B, second tubular element 26 is deflected around connecting portion 38.

Typically, in the locking configuration of device 22, one or more of the following are true:

(1) second end 13 of the second tubular element is disposed closer to first end 10 of the first tubular element than is first end 12 of the second tubular element, (2) first end 12 of the second tubular element is disposed distally (i.e., with respect to the operating physician) to second end 13 of the second tubular element, and (3) at least a quarter of second tubular element 26 is disposed inside lumen L1 of the first tubular element.

In the locking configuration, sutures 34a and 34b are generally not slidable through device 22, i.e., through lumens L1 and L2 of tubular elements 24 and 26. That is, in the locking configuration, the device is fixedly coupled to the sutures, i.e., is generally not slidable over the sutures. Typically, the device is fixedly coupled to the sutures by sandwiching at least part of the sutures between the two tubular elements, e.g., between the outer edge of second tubular element 26 and the inner edge first tubular element 24, as shown at coupling zone 31 in FIG. 2B.

As described hereinabove, device 22 (i.e., the tubular elements and coupling portion thereof) typically comprises a single piece of material that has been fabricated into at least one helix. Typically, device 22 comprises a shape-memory material, which is configured to be biased (e.g., is shape-set) such that the device moves toward the locking configuration thereof. For such applications, the device is retained in the unlocked configuration by at least one constraint 28 (see FIGS. 1A-B), which provides a constraining force. That is, the locking configuration is an unconstrained locking configuration, and the unlocked configuration is a constrained unlocked configuration.

For some applications, and as shown in FIGS. 1A-B, the constraint comprises a rod 30, and the constraining force is provided by the distal end of the rod being disposed in lumen L2 of second tubular element 26. So as to move device 22 into the locking configuration (e.g., so as to fixedly couple the device to the sutures), the surgeon removes the constraining force, e.g., by removing the constraint, such as by withdrawing rod 30 from at least lumen L2, such that the device automatically moves to the locking configuration.

For applications of the invention in which device 22 is constrained in the unlocked configuration by rod 30, rod 30 is typically shaped to define a lumen, and the sutures are slidable through the device by being slidable through the lumen of the rod.

For some applications, device 22 is constrained in the unlocked configuration by a constraining sheath (not shown) for delivery to an intracorporeal site. At, or in the vicinity of, the intracorporeal site, the device is exposed from the delivery sheath and automatically moves into the locking configuration.

Reference is made to FIGS. 3-7, which are schematic illustrations showing the use of apparatus 20 to treat a condition (e.g., regurgitation or leaflet prolapse) of a cardiac valve 4 of a heart 2 of a patient, in accordance with some applications of the invention. FIGS. 3-7 show valve 4, comprising a tricuspid valve 94, being treated via an inferior vena cava 3 of the patient (e.g., transfemorally). However, the scope of the invention includes the treatment of other heart valves and the use of other access routes, mutatis mutandis. In brief (1) distal ends of sutures 34a and 34b are coupled to two sites on annulus 5 of valve 4, (2) the sutures are placed under tension with respect to each other so as to draw the sites on the annulus toward each other, (3) apparatus is used to secure the sutures in the under-tension configuration, and (4) the sutures are cut and released, so as to leave the sutures under tension and the valve in the drawn-together configuration.

FIG. 3 shows a catheter 46 having been advanced through the inferior vena cava and into the right atrium 7 of the heart of the patient. Via catheter 46, a first helical anchor 40a, coupled to a distal end of suture 34a is coupled to (i.e., screwed into) a first site 6 on annulus 5. Typically, anchor 40a is delivered via a first inner sheath 44a. Subsequently, and as shown in FIG. 4, a second helical anchor 40b, coupled to a distal end of suture 34b is coupled to a second site 8 on annulus 5. Typically, second site 8 is at least 1 cm from first site 6, such as a quarter of the way around annulus 5 from the first site, such as on the opposite side of the annulus to the first site.

For some applications in which cardiac valve 4 comprises tricuspid valve 94, first site 6 is typically in a vicinity of an anterior-posterior commissure (APC) 88 (i.e., the commissure between anterior leaflet 82 and posterior leaflet 84) of the valve, and second site 8 is in a vicinity of the septal leaflet of the valve.

Typically, anchor 40b is delivered via a second inner sheath 44b. Alternatively, anchors 40a and 40b are delivered via the same inner sheath.

Figure 5:
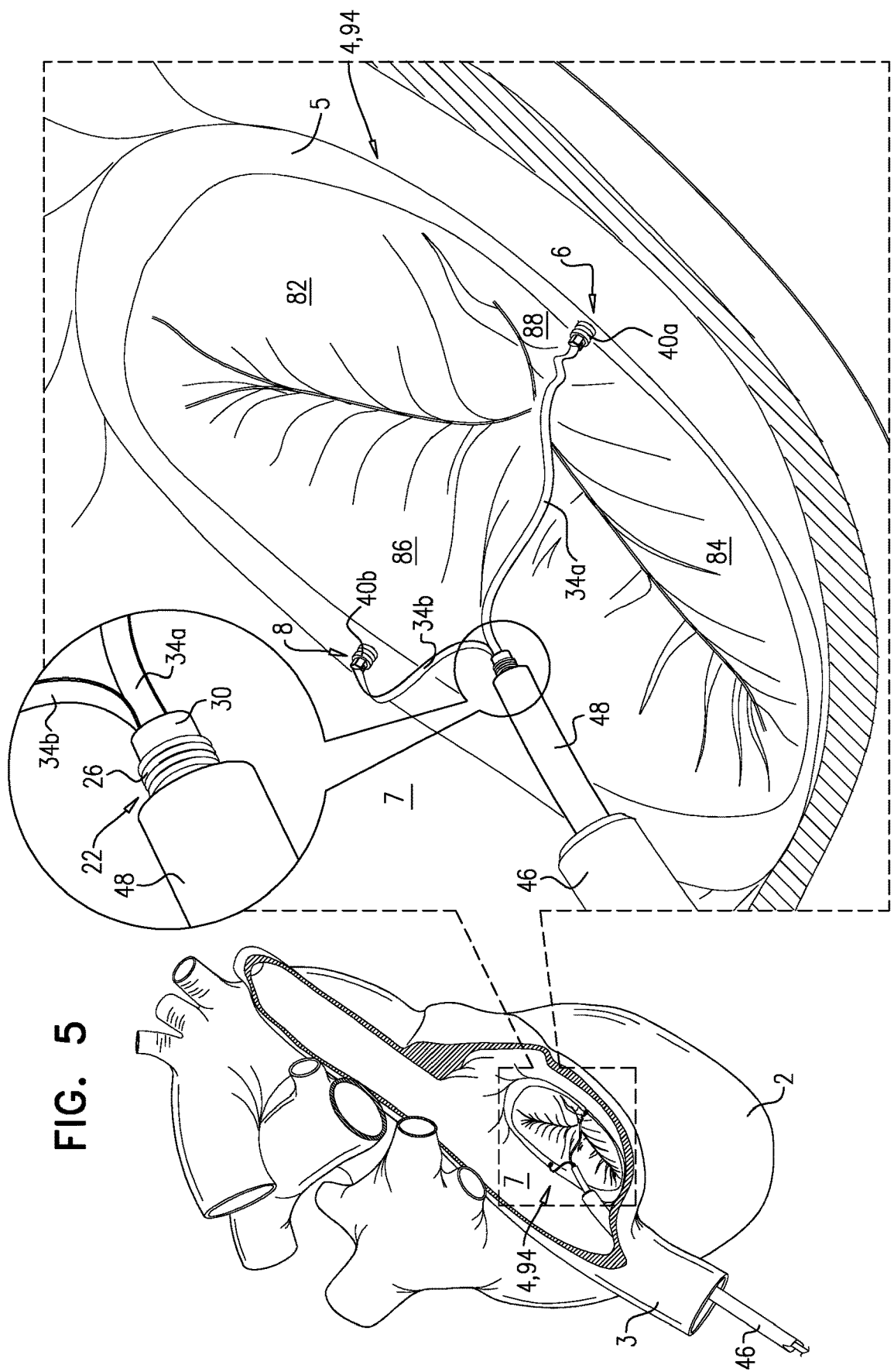

FIG. 5 shows apparatus 20, comprising suture-securing device 22, having been advanced through catheter 46. For some applications, and as shown in FIG. 5, device 22 is delivered via an outer sheath 48. Device 22 is typically delivered in the unlocked configuration thereof, and is typically constrained in the unlocked configuration by rod 30, as described hereinabove. Rod 30 and device 22 are slid over at least part of sutures 34a and 34b. For example, the sutures and helical anchors may be delivered via the lumen of rod 30 (e.g., inner sheaths 44a and 44b may be advanced through the lumen of rod 30).

Figure 6:
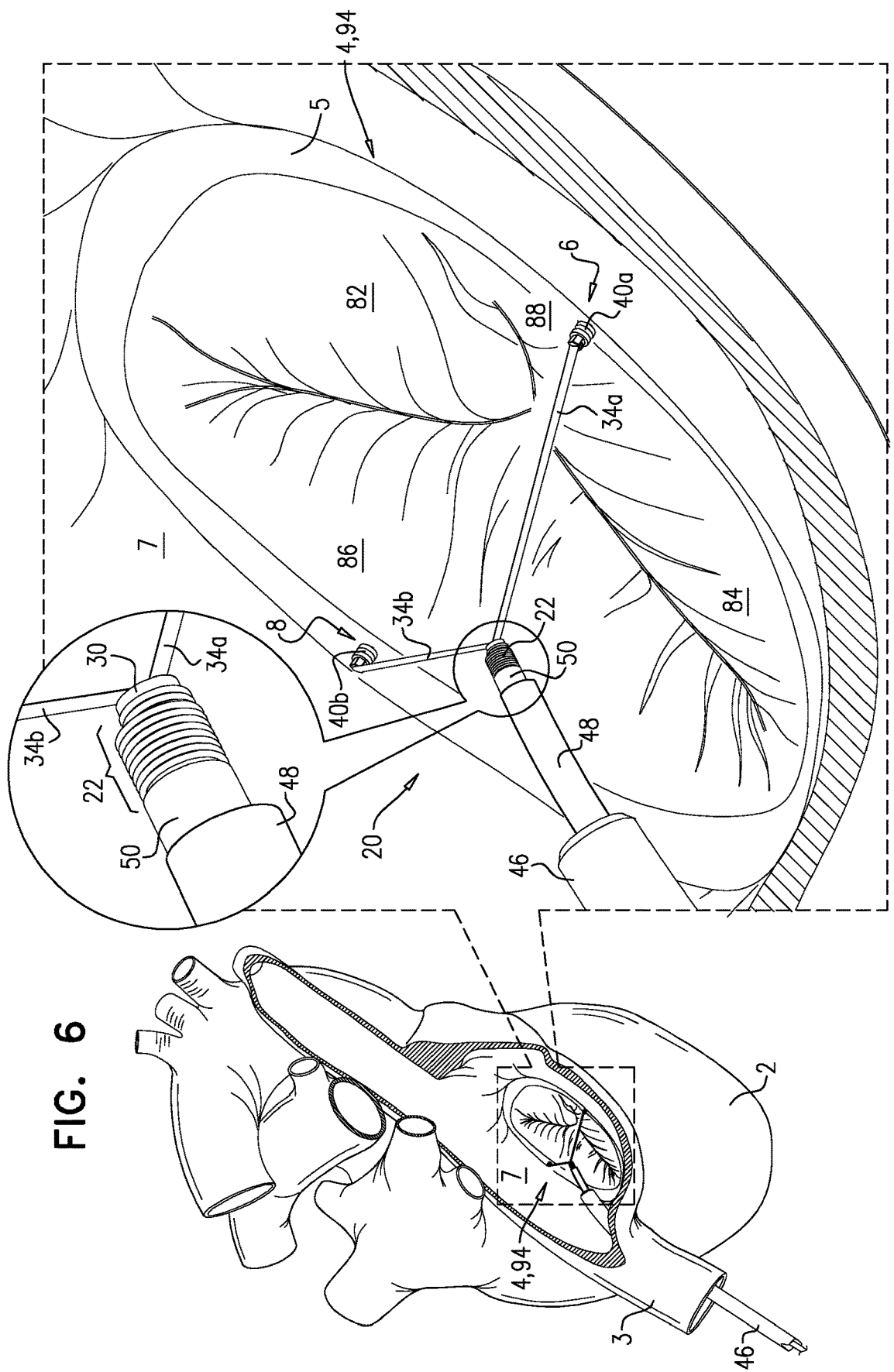

FIG. 6 shows sutures 34a and 34b having been placed under tension at least with respect to each other, e.g., by pulling respective proximal ends of the sutures proximally and/or by pushing device 22 distally, such as by using a controller 50. The tension draws together anchors 40a and 40b, and thereby draws together sites 6 and 8. Thereby, the annulus of valve 4 is reshaped, so as to treat valve prolapse. This reshaping is typically monitored in real-time (e.g., using ultrasound techniques) so that the operating physician may determine when acceptable reshaping has been achieved.

Figure 7:
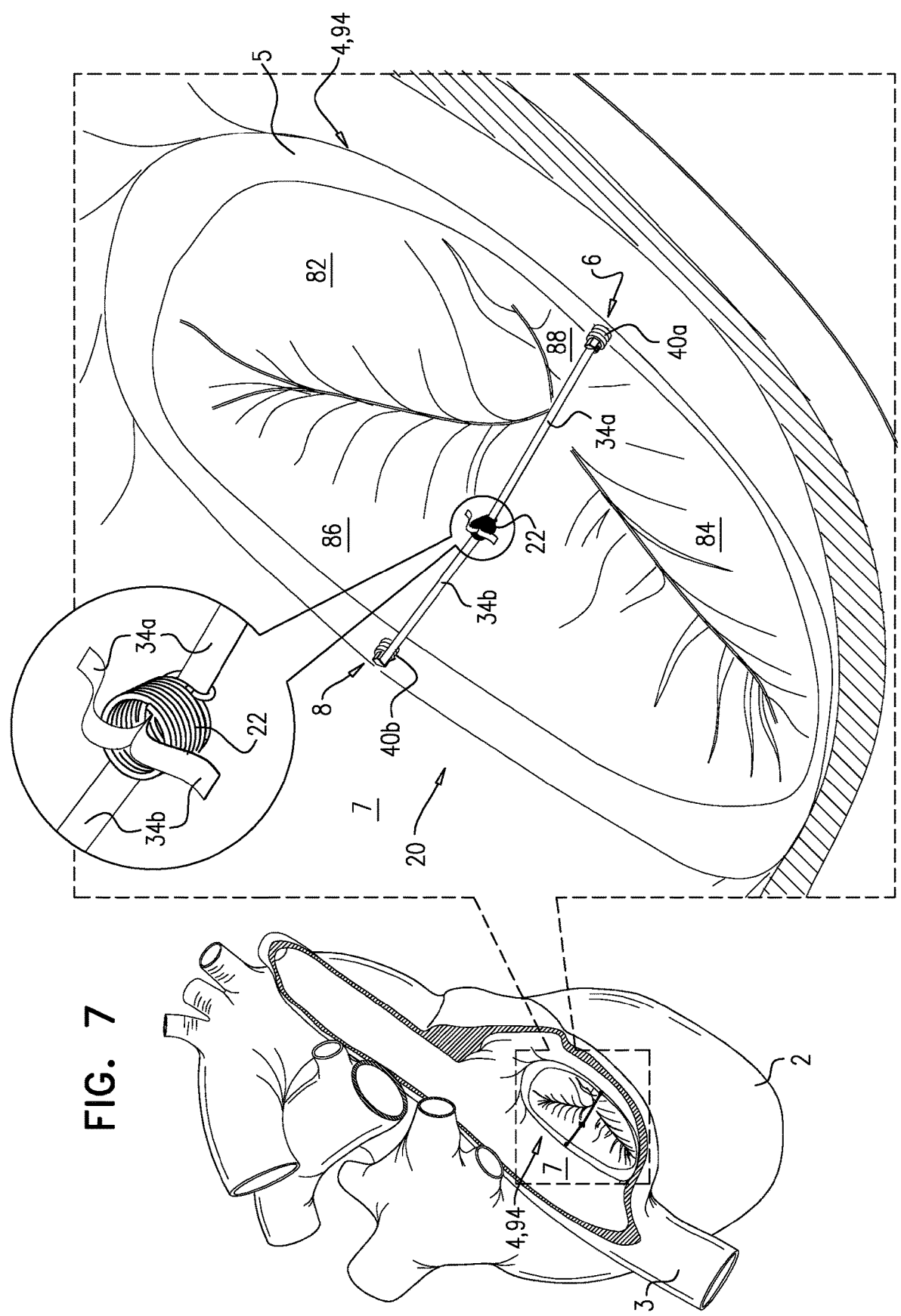

Reference is now made to FIG. 7. Once the operating physician determines that acceptable reshaping has been achieved, device 22 is moved into the locking configuration, e.g., by withdrawing rod 30 proximally. Typically, sutures 34a and 34b are subsequently released, e.g., by being cut at a proximal side of device 22. Rod 30 and the sheaths and catheter are subsequently removed from the body of the patient.

Reference is made to FIGS. 8A-B and 9A-B, which are schematic illustrations of a suture-securing device 60, in accordance with some applications of the invention. Device 60 has an unlocked configuration in which one or more sutures are generally slidable through the device, and a locking configuration in which the sutures are generally not slidable through the device, and is movable from the unlocked configuration to the locking configuration.

FIGS. 8A-B show device 60 in the unlocked configuration thereof. FIG. 8A shows a perspective view of device 60 being used with two sutures 34a and 34b, and FIG. 8B shows a cutaway view of the same. FIG. 8A further shows an exploded view of device 60. It is to be noted that, although device 60 is shown being used with two individual sutures, the device may be used with two portions of the same suture (e.g., the suture is looped), and/or with more or fewer sutures (e.g., to secure the device and/or an element coupled thereto, to a particular point on a single suture).

Device 60 comprises a casing 62, shaped to define a cavity 63 and one or more openings 64, and a core 66, disposed in cavity 63, and shaped to define a lumen L3 therethrough. Typically, casing 62 defines two openings 64. Typically, cavity 63 is open at a lateral side of the casing. Core 66 is movable, at least in part, within cavity 63. Typically, a pin 70 is disposed through casing 62 and core 66, such that core 66 is movable within cavity 63 without decoupling from casing 62. For example, and as shown in FIGS. 8A-9B, core 66 may be shaped to define a socket 74 that has a transverse cross-sectional shape that is larger than a transverse cross-sectional shape of pin 70. Pin 70 is fixedly coupled to casing 62 and movably-coupled, via socket 74, to core 66. Due to the difference in size between the respective cross-sectional shapes of pin 70 and socket 74, core 66 is movable within cavity 63 without decoupling from casing 62.

In the unlocked configuration of device 60, lumen L3 is typically aligned between openings 64, i.e., the lumen is typically disposed on an axis between the openings. Typically, thereby, in the unlocked configuration, lumen L3 is generally in fluid communication with openings 64.

In the unlocked configuration, sutures 34a and 34b are slidable through device 60, i.e., through openings 64 and lumen L3. That is, in the unlocked configuration, the device is slidably coupled to the sutures, i.e., is slidable over the sutures. Typically, device 60 is delivered to an anatomical site (e.g., in a vicinity of a site being treated) with sutures 34a and 34b pre-threaded through the device.

Figure 9B:
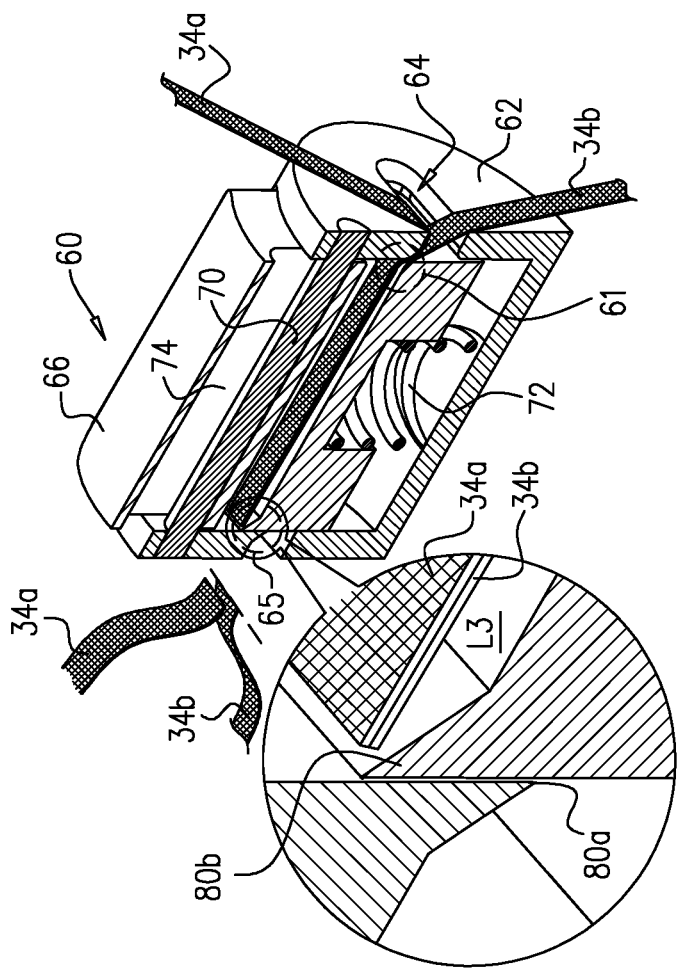
Figure 9A:
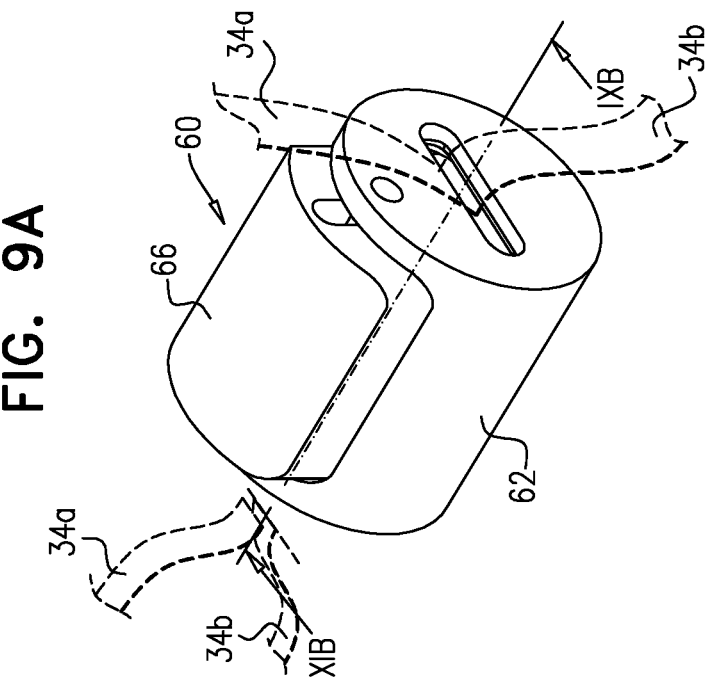

Device 60 typically further comprises and/or defines one or more cutting edges, such as cutting edges 80a and 80b, described further with reference to FIGS. 9A-B.

FIGS. 9A-B show device 60 in the locking configuration thereof, i.e., after having moved into the locking configuration. FIG. 9A shows a perspective view of device 60 being used with two sutures 34a and 34b, and FIG. 9B shows a cutaway view of the same. In the locking configuration of device 60, lumen L3 is typically not aligned between openings 64, i.e., the lumen is typically not disposed on an axis between the openings. Typically, thereby, in the locking configuration, lumen L3 is generally not in fluid communication with openings 64.

In the locking configuration, sutures 34a and 34b are generally not slidable through device 60, i.e., through openings 64 and lumen L3. That is, in the locking configuration, the device is fixedly coupled to the sutures, i.e., is generally not slidable over the sutures. Typically, the device is fixedly coupled to the sutures by sandwiching at least part of the sutures between core 66 and casing 62, as shown at coupling zone 61 in FIG. 9B.

When device 60 moves into the locking configuration, the device cuts the sutures disposed therein, at a cutting zone 65. Typically, a first cutting edge 80a is defined by casing 62, a second cutting edge 80b is defined by core 66, and when sutures 34a and 34b are slid through device 60, part of each suture is disposed between the two cutting edges. When device 60 moves into the locking configuration, the two cutting edges move toward and, typically, past each other, thereby cutting the sutures.

A portion of each suture typically remains within device 60 subsequent to the fixed-coupling of the device to the sutures. For example, and as shown in FIG. 9B, coupling zone 61 may be disposed close to one end of device 60 (e.g., in a vicinity of one opening 64), and cutting zone 65 may be disposed close to another end of the device (e.g., in a vicinity of the other opening 64).

Device 60 is typically configured to be biased such that the device moves toward the locking configuration thereof. Typically, device 60 is thus configured by comprising at least one spring 72, which moves core 66 with respect to casing 62. For such applications, the device is retained in the unlocked configuration by at least one constraint, which provides a constraining force. That is, the locking configuration is an unconstrained locking configuration, and the unlocked configuration is a constrained unlocked configuration.

For example, a portion of core 66 may protrude from a lateral surface of casing 62 when the device is in the locking configuration, and the constraint may comprise a delivery sheath (not shown), which inhibits that portion of core 66 from protruding thus. So as to move device 60 into the locking configuration (e.g., so as to fixedly couple the device to the sutures, and to cut the sutures), the operating physician removes the constraining force, e.g., by removing the constraint, such as by withdrawing the sheath, such that the device automatically moves to the locking configuration.

Figure 10:
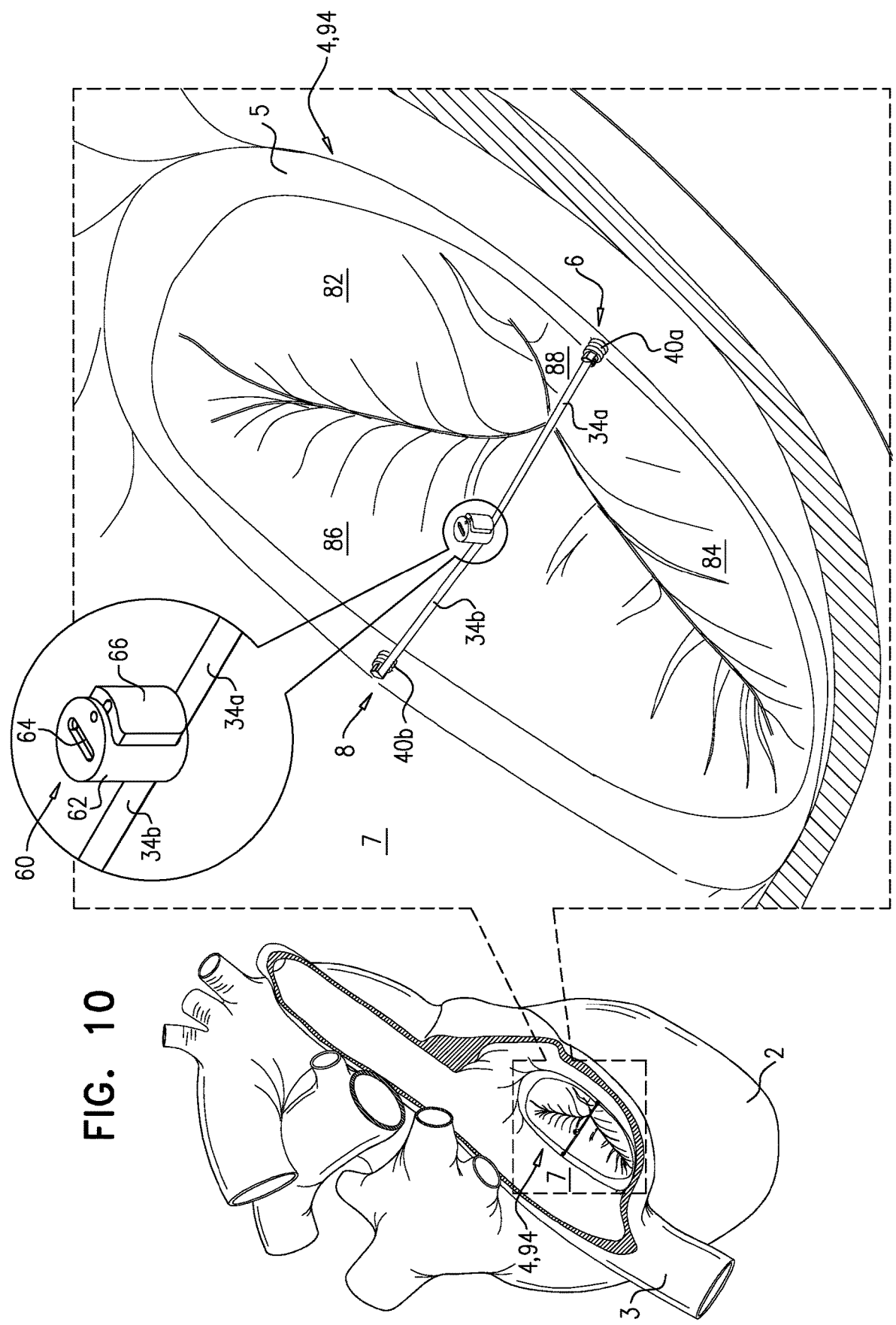
FIG. 10 is a schematic illustration of the suture-securing device of FIGS. 8A-B and 9A-B, having been used to repair a cardiac valve, in accordance with some applications of the invention.

Reference is made to FIG. 10, which is a schematic illustration showing device 60 having been used to treat prolapse in cardiac valve 4, in accordance with some applications of the invention. Typically, device 60 is used in combination with the techniques described with reference to FIGS. 3-7, mutatis mutandis. FIG. 10 shows sutures 34a and 34b having been (1) coupled to annulus 5 at sites 6 and 8, using helical anchors 40a and 40b, (2) fixedly coupled to apparatus 60 and, thereby to each other, and (3) cut using apparatus 60.

Reference is made to FIGS. 11A-14, which are schematic illustrations of a system 100 for repairing heart valve 4, and steps in the use of the system for repairing the heart valve, in accordance with some applications of the invention. System 100 comprises a support 102 and a plurality of leaflet-piercing elements 106, configured to couple the support to the heart valve by piercing the leaflets of the heart valve and coupling to the support. Typically, leaflet-piercing elements 106 are deliverable to the valve independently of support 102.

Typically, system 100 comprises a securing element 104, which comprises elements 106. Securing element 104 typically further comprises a core 108 and a plurality of arms 110. A respective inner end of each arm 110 is coupled to core 108, from which the arms extend radially. Elements 106 are coupled to respective outer ends of each arm. Typically, securing element 104 is deliverable to the valve independently of support 102.

Coupling of securing element 104 to support 102 is facilitated by leaflet-piercing elements 106. Typically, support 102 has an inner perimeter 114 that defines an opening 115, and coupling of securing element 104 to support 102 is further facilitated by at least part of core 108 of element 104 being disposed within opening 115. Typically, core 108 is shaped to define a coupling portion 109, which secures the core within the opening. For example, coupling portion 109 may comprise, or be shaped to define, a ridge 111 which inhibits the core from being decoupled from opening 115 (e.g., coupling portion 109 locks core 108 to support 102).

FIG. 11A shows support 102 and securing element 104 individually, and FIG. 11B shows the securing element coupled to the support.

Typically, support 102 comprises a braided wire mesh, which, when unconstrained, has an expanded configuration, and can be compressed into a compressed configuration. Typically, support 102 is compressed into the compressed configuration for delivery to the heart valve, is constrained in the compressed configuration by a catheter via which the support is delivered, and automatically expands upon being released from a distal end of the catheter at the heart valve. Typically, in the compressed configuration, the support is generally cylindrical in shape. In the uncompressed configuration, support 102 defines a leaflet-engaging side 118 (typically a downstream side of the support) that is typically a flat side. In the uncompressed configuration, support 102 itself is typically flat. Further typically, in the uncompressed configuration, the support defines two adjacent layers and is generally circular (i.e., disc-shaped).

Typically, securing element 104 has a delivery configuration in which arms 110 are disposed distally to core 108, and is configured to be movable to a deployed configuration following delivery to the heart valve. Typically, element 104 is configured to be constrained in the delivery configuration by a delivery sheath, and to automatically move toward the deployed configuration upon being exposed from the sheath at the heart valve.

FIGS. 11A-14 show apparatus 100, and its use in treating tricuspid valve 94 via inferior vena cava 3 of the patient. However, the scope of the invention includes the treatment of other heart valves and the use of other access routes, mutatis mutandis. Additionally, securing element 104 is shown comprising 6 arms and leaflet-piercing elements, but may comprise other pluralities of arms and leaflet-piercing elements.

FIGS. 12A-F show steps in the use of apparatus 100 to treat (e.g., to repair) valve 4, in accordance with some applications of the invention. A catheter 120 is advanced to the valve; typically to right atrium 7 via inferior pulmonary artery 3 (e.g., transfemorally), as shown in FIG. 12A. FIG. 12B shows a delivery sheath 122 having been advanced out of a distal end of catheter 120 and, via valve 4, to a downstream side of the valve (i.e., into right ventricle 9) of the patient. FIG. 12B further shows securing element 104 having been moved (e.g., advanced distally) out of delivery sheath 122 and into ventricle 9, and expanding into the deployed configuration.

Subsequently, securing element 104 is moved (e.g., pulled) proximally, such that leaflet-piercing elements 106 pierce the leaflets of the valve, thereby coupling the securing element to the leaflets, as shown in FIG. 12C. Securing element 104 is shown comprising six arms and leaflet-piercing elements, and being coupled to the leaflets such that two leaflet-piercing elements pierce (i.e., couple to) each leaflet. It is to be noted that the scope of the present invention includes securing element 104 comprising other pluralities of arms and/or leaflet-piercing elements, and other configurations of coupling to the leaflets.

Subsequently, as shown in FIG. 12D-E, support 102 is delivered to an upstream side of the valve (i.e., into right atrium 7). Typically, support 102 is advanced through catheter 120 and, upon being exposed from the end of the catheter, automatically expands into its expanded configuration. Typically, delivery sheath 122 is typically disposed within opening 115 of the support. That is, perimeter 114 of the support is disposed around delivery sheath 122, which is typically still coupled to securing element 104. For some applications, delivery sheath 122 is coupled to securing element 104 by a lock 124 (see FIG. 13A), which is controllable from outside of the body of the patient. For some such applications, lock 124 is directly coupled to delivery sheath 122. Alternatively, lock 124 is coupled to a controller (e.g., a control wire; not shown) that is disposed within sheath 122.

Figure 13A:
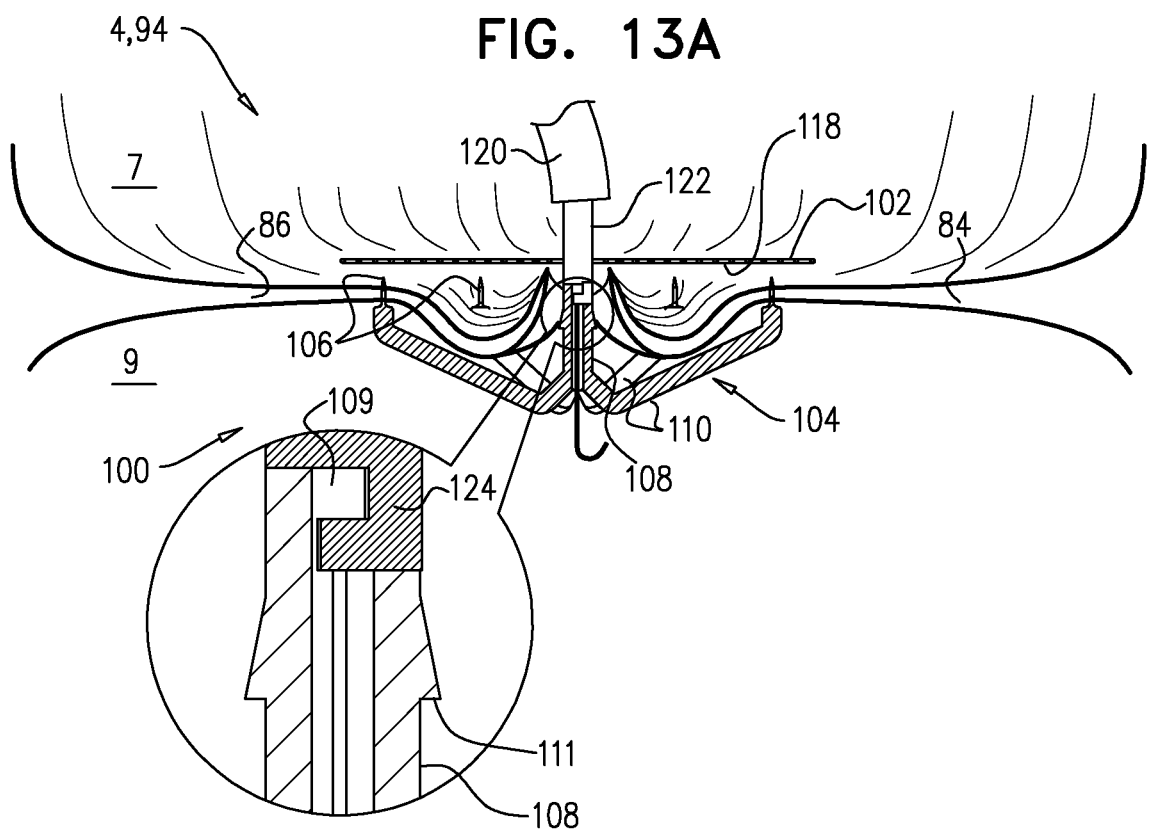

Support 102 is placed against the leaflets of the valve (e.g., leaflet-engaging side 118 of the support is placed against the upstream surface of the leaflets), typically by being slid over delivery sheath 122. That is, delivery sheath 122 typically acts as a guide for support 102. FIG. 12E shows a perspective view, and FIG. 13A shows a respective cutaway view, of support 102 disposed against the leaflets. Typically, support 102 is placed, and is configured to be placed, against the leaflets of the valve such that the support overlaps more than one leaflet. That is, the support is typically placed such that respective portions of the leaflet-engaging side of the support are disposed against respective regions of respective leaflets of the valve.

Figure 13B:
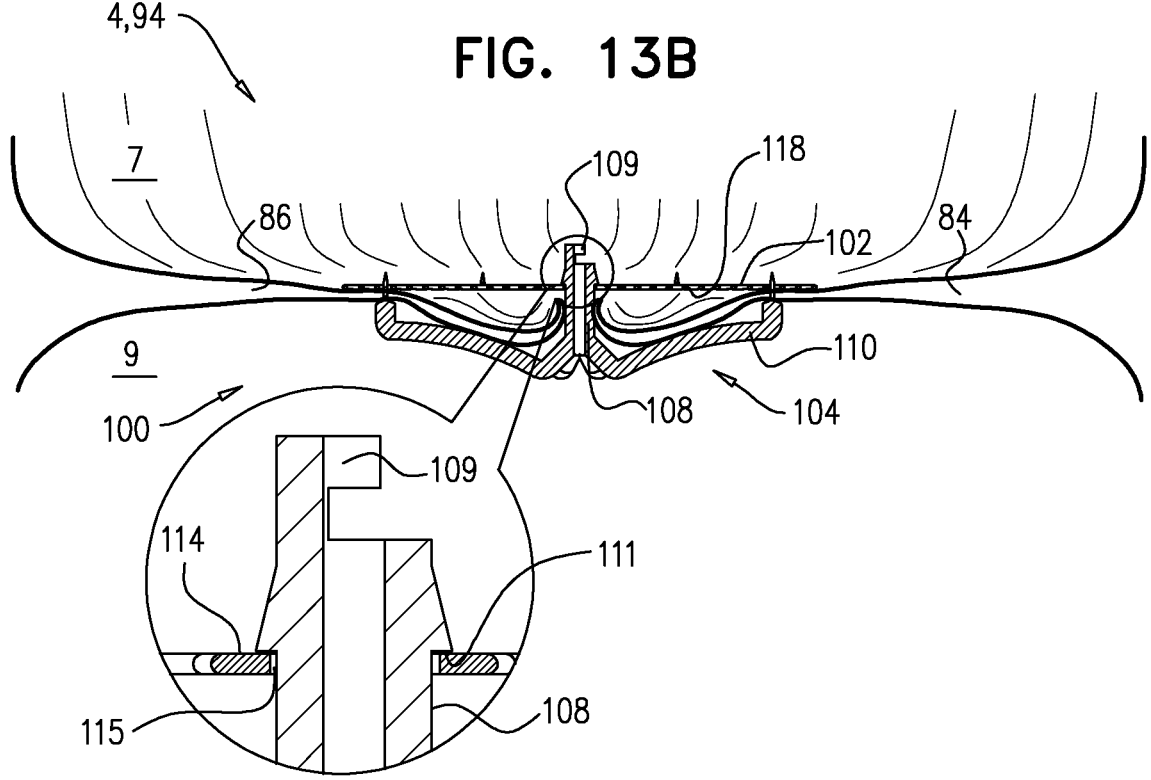

FIGS. 12F and 13B show respective perspective and cutaway views of support 102 having been fixedly coupled to securing element 104, thereby sandwiching the leaflets of the valve between the support and the securing element. Leaflet-piercing elements 106 typically protrude into (e.g., through) support 102. FIGS. 12F and 13B also show catheter 120 and sheath 122 having been removed from the body of the patient. Typically, this fixed coupling is performed by securing element 104 is held immobile or pulled proximally, while support 102 is pushed distally, such that inner perimeter 114 of the support is slid over at least part of core 108 of the coupling element. For example, the support may be slid over coupling portion 109, such that ridge 111 is 'clicked' into place. Typically, support 102 is pushed distally using catheter 120 and/or a separate controller (not shown). If support 102 is pushed using catheter 120, the catheter has an outer diameter that is greater than the diameter of opening 115 of the support.

FIG. 13B shows arms 110 of securing element 104 as being bent compared to the appearance of the arms in FIG. 13A. For some applications of the invention, arms 110 are resilient, and are configured to be bent by the coupling of element 104 to support 102, acting like a spring. This configuration facilitates the coupling of apparatus 100 to the valve leaflets by transferring force from the coupling of coupling portion 109 and perimeter 114, to leaflet-piercing elements 106, thereby holding leaflet-piercing elements 106 within the leaflets and within mesh 112 of support 102. That is, coupling of coupling portion 109 of core 108 to the support facilitates coupling of the leaflet-piercing elements to the support. For some applications of the invention, leaflet-piercing elements 106 comprise straight spikes. For other applications of the invention, leaflet-piercing elements 106 comprise barbs or hooks, so as to facilitate fixed coupling of the leaflet-piercing elements directly to mesh 112.

As shown in FIGS. 12F and 13B, when apparatus 100 is implanted (i.e., coupled to the leaflets of the heart valve), arms 110 of securing element 104 are typically disposed on one side of the valve, and both coupling portion 109 and leaflet-piercing elements 106 are coupled to support 102 on the other side of the valve. Thereby, for some applications, securing element 104 is coupled to support 102 only at the upstream side of the heart valve of the patient.

FIGS. 12A-13B show securing element 104 being moved proximally (i.e., upstream), so as to couple to the valve leaflets, prior to the delivery of support 102. However, for some applications of the invention, support 102 is delivered before moving element 104 proximally.

Figure 14:
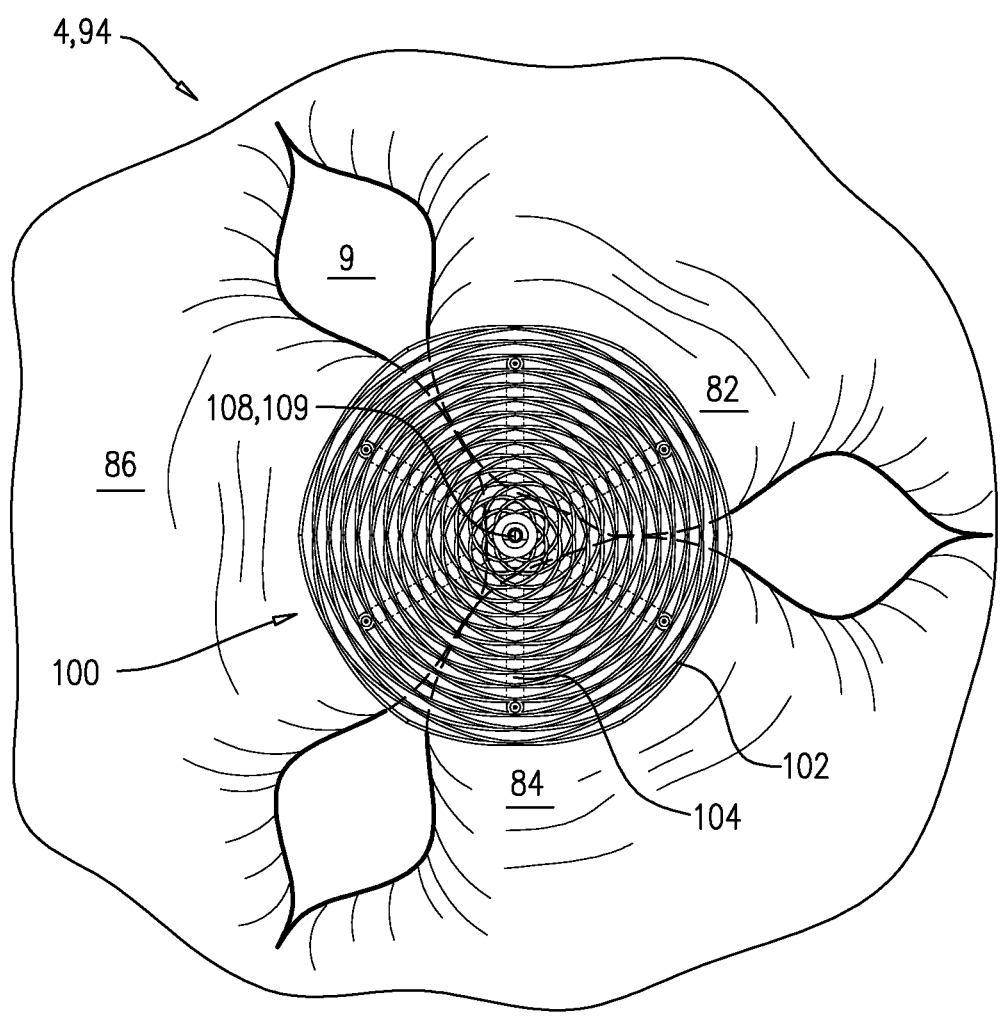

FIG. 14 is an atrial-side view of apparatus 100 having been used to repair valve 4 (e.g., tricuspid valve 94), as described in FIGS. 12A-13B. Support 102 is typically coupled to the leaflets of the valve such that the support overlaps more than one leaflet. That is, the support is typically coupled to the valve such that respective regions of the support are disposed against respective portions of respective leaflets of the valve. The cusps of the leaflets of the valve are typically held close to each other (e.g., touching each other) by apparatus 100, which is thereby disposed generally centrally in the valve. Typically, portions of the leaflets between apparatus 100 and the leaflet commissures (e.g., APC 88) are not held close to each other, and move with the beating of the heart. That is, these portions of the leaflets typically open during ventricular diastole and close during ventricular systole, thereby forming three orifices which typically act as separate valves. FIG. 14 shows these portions of the leaflets open (i.e., during diastole), such that right ventricle 9 is visible therebetween.

For some applications of the invention, support 102 is dimensioned to cover more than 10% and/or less than 90% (e.g., between 10% and 90%, such as between 10% and 30%) of the area defined by the native orifice of the heart valve. For example, a support of desired dimensions may be selected according to the valve and/or patient being treated (e.g., following measurement of the valve being treated).

It is hypothesized that the use of apparatus 100 as described with reference to FIGS. 11-14 reduces heart valve regurgitation, and may be used to repair a diseased heart valve.

Reference is now made to FIG. 15. Although apparatus 100 is shown hereinabove being configured and used, to repair tricuspid valve 94, the apparatus may be configured and used with other heart valves. For example, FIG. 15 shows apparatus 100 having been used to repair a mitral valve 130 of a patient, whereby support 102 is disposed in a right atrium 137 of the patient, and securing element 104 (not visible in FIG. 15) is disposed in a right ventricle 139 of the patient. For a bicuspid heart valve such as mitral valve 130, two orifices are typically formed between apparatus 100 and the commissures.

Apparatus 100 is typically coupled to the heart valve being treated, such that support 102 is disposed against an upstream side of the valve (i.e., an upstream side of the valve leaflets), and securing element 104 is disposed against a downstream side of the valve (i.e., against a downstream side of the valve leaflets). However, for some applications, apparatus 100 is coupled to the heart valve such that support 102 is disposed against the downstream side of the valve, and securing element 104 is disposed against the upstream side of the valve.

Apparatus 100 is typically delivered to the heart valve percutaneously (e.g., transcatheterally and/or transluminally). Apparatus 100 is shown being delivered transluminally from an upstream side of the valve (e.g., via the inferior vena cava). That is, typically, from the perspective of the operating physician, the upstream side of the valve is the proximal side of the valve, and the downstream side of the valve is the distal side of the valve. However, it is to be noted that the scope of the present invention includes delivery from a downstream side of the valve (e.g., transapically, or via the aorta), mutatis mutandis.

Reference is now made to FIGS. 8A-15. Typically, device 60 (FIGS. 8A-10) and system 100 (9A-15) are used in catheter-based procedures or minimally-invasive procedures. For some applications, device 60 (FIGS. 8A-10) and system 100 (9A-15) may be used in a surgical procedure, e.g., an open-heart procedure.

Reference is made to FIGS. 1A-15. It is to be noted that devices 22 and 60, and system 100 described herein may be used in any suitable location in the body of the patient. For example, devices 22 and 60 can be used to secure sutures in any part of the body. Additionally, it is to be noted that devices 22 and 60, and system 100 described herein may be used in any cardiac valve (i.e., the mitral, the tricuspid, the pulmonary, and the aortic valve) of the patient.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A suture-securing device for use with one or more sutures, the suture-securing device comprising:
a first tubular element, shaped to define a first lumen therethrough, and having a first end and a second end; and
a second tubular element, shaped to define a second lumen therethrough, and having a first end and a second end,
wherein the suture-securing device is configured to have:
(a) an unlocked configuration in which:
the first end of the second tubular element is disposed closer to the first end of first tubular element than is the second end of the second tubular element, and
the one or more sutures are disposable within and slidable through the first and second lumens, and
(b) a locking configuration in which:
the second end of the second tubular element is disposed closer to the first end of first tubular element than is the first end of the second tubular element, and
the one or more sutures are inhibited from sliding through the first and second lumens, and
wherein the suture-securing device is configured such that:
in the unlocked configuration, the second end of the second tubular element is disposed outside of the first lumen, and
in the locking configuration, the second end of the second tubular element is disposed within the first lumen.

2. The suture-securing device according to claim 1, wherein the second end of first tubular element is coupled to the first end of the second tubular element.

3. The suture-securing device according to claim 1, wherein the suture-securing device is configured such that, when the one or more sutures are disposed within the lumens of the first and second tubular elements, movement of the suture-securing device from the unlocked to the locking configuration rotates at least a portion of each suture.

4. The suture-securing device according to claim 1, wherein the suture-securing device is configured such that movement of the suture-securing device from the unlocked to the locking configuration rotates the second tubular element.

5. The suture-securing device according to claim 1, wherein the suture-securing device comprises at least one helical element.

6. The suture-securing device according to claim 5, wherein, at least in the unlocked configuration, the suture-securing device defines a continuous helix from the first end of first tubular element to the second end of the second tubular element.

7. The suture-securing device according to claim 1, wherein the second end of first tubular element is coupled to the first end of the second tubular element by a connecting portion.

8. The suture-securing device according to claim 7, wherein the tubular elements and the connecting portion comprise a continuous piece of material.

9. A suture-securing device for use with one or more sutures, the suture-securing device comprising:
a first tubular element, shaped to define a first lumen therethrough, and having a first end and a second end; and
a second tubular element, shaped to define a second lumen therethrough, and having a first end and a second end,
wherein the suture-securing device is configured to have:
(a) an unlocked configuration in which:
the first end of the second tubular element is disposed closer to the first end of first tubular element than is the second end of the second tubular element, and
the one or more sutures are disposable within and slidable through the first and second lumens, and
(b) a locking configuration in which:
the second end of the second tubular element is disposed closer to the first end of first tubular element than is the first end of the second tubular element, and
the one or more sutures are inhibited from sliding through the first and second lumens, and
wherein the second tubular element has a length, from the first end of the second tubular element to the second end of the second tubular element, that is smaller than a cross-sectional diameter of the first lumen.

10. A suture-securing device for use with one or more sutures, the suture-securing device comprising:
a first tubular element, shaped to define a first lumen therethrough, and having a first end and a second end; and
a second tubular element, shaped to define a second lumen therethrough, and having a first end and a second end,
wherein the suture-securing device is configured to have:
(a) an unlocked configuration in which:
the first end of the second tubular element is disposed closer to the first end of first tubular element than is the second end of the second tubular element, and
the one or more sutures are disposable within and slidable through the first and second lumens, and
(b) a locking configuration in which:
the second end of the second tubular element is disposed closer to the first end of first tubular element than is the first end of the second tubular element, and
the one or more sutures are inhibited from sliding through the first and second lumens,
wherein the unlocked configuration is a constrained configuration, and the locking configuration is an unconstrained configuration, and
wherein the suture-securing device is configured to be retained in the constrained unlocked configuration by a constraining force, and to automatically move toward the unconstrained locking configuration when the constraining force is removed.

11. The suture-securing device according to claim 10, wherein the suture-securing device is configured such that:
in the unlocked configuration, the second end of the second tubular element is disposed outside of the first lumen, and
in the locking configuration, the second end of the second tubular element is disposed within the first lumen.

12. A system comprising the suture-securing device according to claim 10, wherein the system further comprises a constraint, configured to provide the constraining force.

13. The system according to claim 12, wherein the constraint comprises a rod, disposable in the lumen of at least one of the tubular elements, configured to provide the constraining force by being disposed in the lumen, the constraining force being removable by removing the rod from the lumen.

14. A suture-securing device for use with one or more sutures, the suture-securing device comprising:
a first tubular element, shaped to define a first lumen therethrough, and having a first end and a second end; and
a second tubular element, shaped to define a second lumen therethrough, and having a first end and a second end,
wherein the suture-securing device is configured to have:
(a) an unlocked configuration in which:
the first end of the second tubular element is disposed closer to the first end of first tubular element than is the second end of the second tubular element, and
the one or more sutures are disposable within and slidable through the first and second lumens, and
(b) a locking configuration in which:
the second end of the second tubular element is disposed closer to the first end of first tubular element than is the first end of the second tubular element, and
the one or more sutures are inhibited from sliding through the first and second lumens, and
wherein the first and second tubular elements both define respective inner and outer surfaces, and wherein, in the locking configuration, at least part of the outer surface of the second tubular element is disposed against at least part of the inner surface of first tubular element.

15. The suture-securing device according to claim 14, wherein the suture-securing device is configured such that, when the one or more sutures are disposed within the lumens of the first and second tubular elements, movement of the suture-securing device from the unlocked to the locking configuration sandwiches at least a portion of each suture between the outer surface of the second tubular element and the inner surface of first tubular element.

16. A suture-securing device for use with one or more sutures, the suture-securing device comprising:
a first tubular element, shaped to define a first lumen therethrough, and having a first end and a second end; and
a second tubular element, shaped to define a second lumen therethrough, and having a first end and a second end,
wherein the suture-securing device is configured to have:
(a) an unlocked configuration in which:
the first end of the second tubular element is disposed closer to the first end of first tubular element than is the second end of the second tubular element, and
the one or more sutures are disposable within and slidable through the first and second lumens, and
(b) a locking configuration in which:
the second end of the second tubular element is disposed closer to the first end of first tubular element than is the first end of the second tubular element, and
the one or more sutures are inhibited from sliding through the first and second lumens, and
wherein the suture-securing device is configured such that:
in the unlocked configuration, at least a quarter of the second tubular element is disposed outside of the first lumen, and
in the locking configuration, at least a quarter of the second tubular element is disposed inside the first lumen.

17. A suture-securing device for use with one or more sutures, the suture-securing device comprising:
a first tubular element, shaped to define a first lumen therethrough, and having a first end and a second end; and
a second tubular element, shaped to define a second lumen therethrough, and having a first end and a second end,
wherein the suture-securing device is configured to have:
(a) an unlocked configuration in which:
the first end of the second tubular element is disposed closer to the first end of first tubular element than is the second end of the second tubular element, and
the one or more sutures are disposable within and slidable through the first and second lumens, and
(b) a locking configuration in which:
the second end of the second tubular element is disposed closer to the first end of first tubular element than is the first end of the second tubular element, and
the one or more sutures are inhibited from sliding through the first and second lumens, wherein the second tubular element is coupled to first tubular element at a coupling point, the coupling point being configured to facilitate deflection of the second tubular element around the coupling point, wherein the suture-securing device is configured:
   to be constrainable in the unlocked configuration by a constraining force, and
   when the constraining force is removed, to automatically move from the unlocked configuration to the locking configuration, by the second tubular element deflecting around the coupling point.

18. The suture-securing device according to claim 17, wherein the first and second tubular elements both define respective inner and outer surfaces, and wherein, in the locking configuration, at least part of the outer surface of the second tubular element is disposed against at least part of the inner surface of first tubular element.

19. The suture-securing device according to claim 18, wherein the suture-securing device is configured such that, when the one or more sutures are disposed within the lumens of the first and second tubular elements, the deflecting of the second tubular element around the coupling point sandwiches at least a portion of each suture between the outer surface of the second tubular element and the inner surface of first tubular element.

* * * * *